(12) United States Patent
Tamura

(10) Patent No.: US 8,480,590 B2
(45) Date of Patent: *Jul. 9, 2013

(54) METHODS AND APPARATUS FOR ULTRASOUND IMAGING

(75) Inventor: Tadashi Tamura, North Haven, CT (US)

(73) Assignee: Hitachi Aloka Medical, Ltd., Tokyo (JP)

(*) Notice: Subject to any disclaimer, the term of this patent is extended or adjusted under 35 U.S.C. 154(b) by 340 days.

This patent is subject to a terminal disclaimer.

(21) Appl. No.: 12/854,851

(22) Filed: Aug. 11, 2010

(65) Prior Publication Data

US 2011/0040188 A1 Feb. 17, 2011

Related U.S. Application Data

(60) Provisional application No. 61/232,862, filed on Aug. 11, 2009.

(51) Int. Cl.
| A61B 8/14 | (2006.01) |
| G01S 13/95 | (2006.01) |
| G09G 5/02 | (2006.01) |
| G01F 1/66 | (2006.01) |

(52) U.S. Cl.
USPC ......... 600/457; 600/453; 600/454; 342/26 D; 345/589; 73/861.25

(58) Field of Classification Search
None
See application file for complete search history.

(56) References Cited

U.S. PATENT DOCUMENTS

| 4,913,159 | A | * | 4/1990 | Gardin et al. | 600/456 |
| 5,027,122 | A | * | 6/1991 | Wieler | 342/26 D |
| 5,123,417 | A | * | 6/1992 | Walker et al. | 600/455 |
| 5,383,463 | A | * | 1/1995 | Friedman | 600/455 |
| 6,177,923 | B1 | * | 1/2001 | Arenson et al. | 345/589 |
| 6,719,697 | B2 | * | 4/2004 | Li | 600/454 |
| 7,044,913 | B2 | * | 5/2006 | Shiki | 600/454 |
| 8,088,069 | B2 | * | 1/2012 | Sabata | 600/437 |
| 8,142,361 | B2 | * | 3/2012 | Zhang et al. | 600/455 |
| 8,435,182 | B1 | * | 5/2013 | Tamura | 600/454 |
| 2002/0151794 | A1 | * | 10/2002 | Li | 600/454 |
| 2003/0045797 | A1 | * | 3/2003 | Christopher et al. | 600/453 |
| 2003/0125624 | A1 | * | 7/2003 | Shiki | 600/443 |
| 2004/0102706 | A1 | * | 5/2004 | Christopher et al. | 600/453 |
| 2005/0090747 | A1 | * | 4/2005 | Clark | 600/453 |
| 2006/0184032 | A1 | * | 8/2006 | Shiki | 600/454 |

(Continued)

OTHER PUBLICATIONS

Wuest et al, "A Variational De-Aliasing Technique", Phys Chem Earth. vol. 25, No. 10-12, pp. 1179-1183, 2000.*

(Continued)

Primary Examiner — Long V. Le
Assistant Examiner — Angela M Hoffa
(74) Attorney, Agent, or Firm — Buckley, Maschoff & Talwalkar LLC

(57) ABSTRACT

Some embodiments include acquisition of color Doppler data, and detection of one or more transitions of the color Doppler data, each of the one or more transitions being between a first area representing flow velocity in a first direction and a second area representing flow velocity not in the first direction. A normalized energy function across one or more of the one or more transitions is calculated, a configuration of flow areas within the color Doppler data is determined, and aliasing corrections for the color Doppler data are determined based on the normalized energy functions and the configuration of flow areas.

40 Claims, 15 Drawing Sheets

U.S. PATENT DOCUMENTS

| | | | |
|---|---|---|---|
| 2007/0167770 A1* | 7/2007 | Miyaki | 600/437 |
| 2007/0255138 A1* | 11/2007 | Kristofferson et al. | 600/443 |
| 2008/0242994 A1* | 10/2008 | Tamura | 600/453 |
| 2009/0043208 A1* | 2/2009 | Hergum et al. | 600/455 |
| 2009/0087056 A1 | 4/2009 | Fu et al. | |
| 2011/0015526 A1* | 1/2011 | Tamura | 600/453 |
| 2012/0179047 A1* | 7/2012 | Zhang et al. | 600/455 |

OTHER PUBLICATIONS

"Patent Cooperation Treaty: PCT International Search Report", dated Apr. 12, 2011 for PCT/US2010/045233, 3pgs.

* cited by examiner

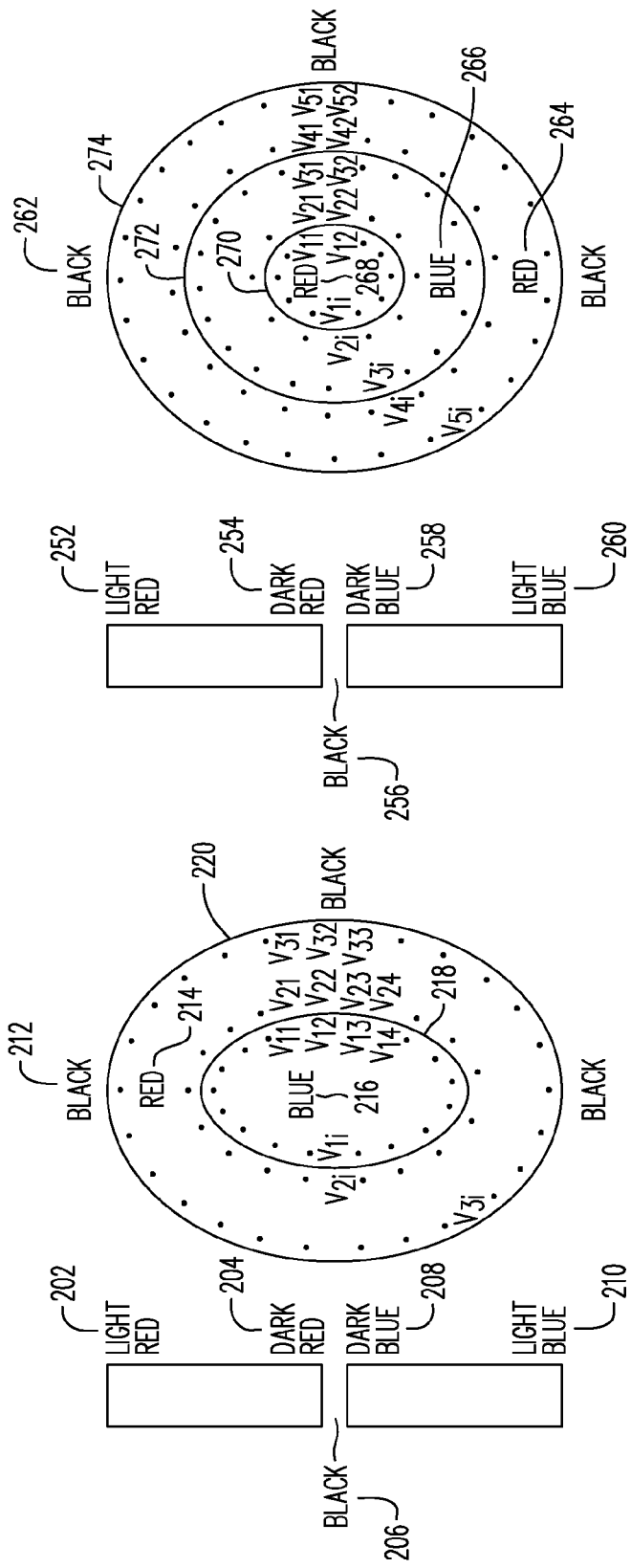

METHODS AND APPARATUS FOR ULTRASOUND IMAGING

CROSS-REFERENCE TO RELATED APPLICATION

The present application claims priority to U.S. Provisional Patent Application Ser. No. 61/232,862, filed on Aug. 11, 2009 and entitled "Method and Apparatus for Ultrasound Imaging", the contents of which are incorporated herein by reference for all purposes.

BACKGROUND

Systems and methods described herein generally relate to the field of ultrasound imaging. More specifically, embodiments described below relate to methods and systems for color flow imaging.

Ultrasound is used to image various internal structures, including but not limited to the heart, the liver, a fetus, and blood vessels. For diagnosis of cardiovascular diseases, color Doppler (or color flow) imaging is usually used to visualize blood flow in the heart or blood vessels. Abnormal conditions often increase blood flow velocity in comparison to that under normal conditions. The increased velocity may result in aliasing within a corresponding color Doppler image. Color Doppler uses a pulse ultrasound technology for its spatial sampling capability, which limits the maximum velocity which can be detected without experiencing aliasing. The pulse repetition frequency (PRF), which is also the sampling frequency, sets the maximum frequency limitation. This limitation, in turn, limits the maximum blood flow velocity which can be measured without exhibiting aliasing. This limitation may be particularly problematic in cardiac cases. For example, the PRF cannot be set high enough to measure abnormally high blood velocities that occur at substantial imaging depths such as, for example, regurgitation jets across heart valves. Therefore, under abnormal cardiac conditions, color Doppler often exhibits aliasing, thereby reducing the reliability of any diagnosis based on the blood flow image. Thus, there exists a need to address this aliasing problem.

SUMMARY

Some embodiments include acquisition of color Doppler data, and detection of one or more transitions of the color Doppler data, each of the one or more transitions being between a first area representing flow velocity in a first direction and a second area representing flow velocity not in the first direction. A normalized energy function across one or more of the one or more transitions is calculated, a configuration of flow areas within the color Doppler data is determined, and aliasing corrections for the color Doppler data are determined based on the normalized energy functions and the configuration of flow areas.

BRIEF DESCRIPTION OF THE DRAWINGS

FIG. 2A: Color Doppler image with two flow areas.
FIG. 2B: Color Doppler image with three flow areas.

DETAILED DESCRIPTION

Figure 1B:
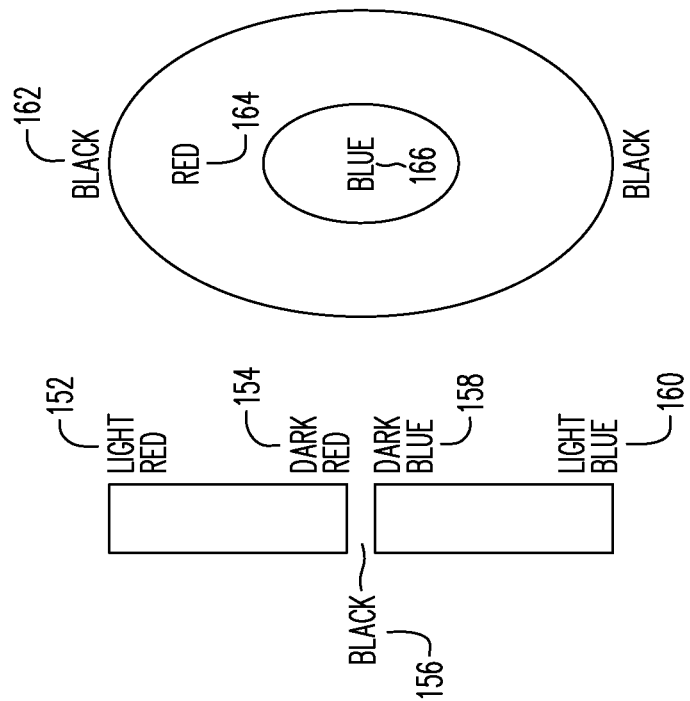
FIG. 1B: Color Doppler image with two flow areas.

Embodiments will be described with reference to the accompanying drawing figures wherein like numbers represent like elements throughout. Before these embodiments are explained in detail, it is to be understood that embodiments are not limited in their application to the details of the examples set forth in the following description or illustrated in the figures. Other embodiments may be practiced or carried out in a variety of applications and in various ways. Also, it is to be understood that the phraseology and terminology used herein is for the purpose of description and should not be regarded as limiting. The use of "including," "comprising," or "having," and variations thereof herein is meant to encompass the items listed thereafter and equivalents thereof as well as additional items. The terms "mounted," "connected," and "coupled," are used broadly and encompass both direct and indirect mounting, connecting, and coupling. Further, "connected," and "coupled" are not restricted to physical or mechanical connections or couplings.

It should be noted that embodiments are not limited to any particular software language described or that is implied in the figures. One of ordinary skill in the art will understand that a variety of alternative software languages may be used for implementation of some embodiments. It should also be understood that some of the components and items are illustrated and described as if they were hardware elements, as is common practice within the art. However, one of ordinary skill in the art, and based on a reading of this detailed description, would understand that, in at least one embodiment, components in the method and system may be implemented in software or hardware.

An ultrasound transducer transmits ultrasound (i.e., ultrasonic waves) into a human body to image various internal structures, including but not limited to blood vessels, a fetus, and the heart. Scatterers in tissue scatter the ultrasound and the scattered ultrasound is returned to the transducer. A receive beamformer creates ultrasound beams and a post-processor creates an image of tissues from the amplitude of the returned ultrasound signal as a B-mode image.

Blood vessels or the heart are often imaged, since they indicate cardiovascular conditions of patients. Blood flow information is usually acquired using color Doppler and spectral Doppler techniques.

Color Doppler is a two-dimensional imaging technique commonly used for imaging blood flow by sending ultrasonic waves into the blood flow and detecting the scattered ultrasound from the moving red cells. It consists of many beams similar to a B-mode image. A description of a color Doppler technique now follows; embodiments are not limited to the specific details therein.

In order to detect flow velocity, an ultrasound transducer transmits ultrasound signals several times per position to detect motion. To create a two-dimensional flow image, the transmit position is shifted by sub-millimeters, or about the order of an ultrasound wavelength. The transmit position shifting is repeated about 100 times to cover several centimeters and to create a two-dimensional flow image in linear and convex formats. For a phased array transducer or a sector image format, the transmit direction is changed a small angle, for example, about 0.5-1.0 degrees. This is repeated approximately 100 times to cover about 90 degrees of a sector image. For each transmit position or direction, ultrasound is transmitted several times. Received beamformed RF ultrasound signals undergo quadrature demodulation resulting in complex, Doppler I-Q signals.

In a color Doppler technique, the ultrasound is transmitted at a pulse repetition frequency (PRF) and the blood flow velocity is detected as the shift in frequency (Doppler shift frequency) in the received ultrasound signal. The received ultrasound is mixed with in-phase (0 degrees) and quadrature (90 degrees) reference signals of the same frequency as the transmit ultrasound frequency. After low-pass filtering high frequency components (e.g., second harmonics), only the baseband signals are obtained. Wall filtering (i.e., high-pass filtering) is applied to the baseband signals to remove strong clutter noise from tissue and slowly moving tissues such as blood vessel walls, resulting in complex I-Q Doppler signals. The wall filtering is performed because the Doppler I-Q signals may contain blood flow signal components as well as stationary tissue signal components. The stationary components are typically 30-40 dB greater than the blood flow components. Therefore, it is desirable to reduce or eliminate the stationary signal components in order to detect blood flow accurately.

Generally, the wall-filtered complex I-Q signal is used to derive the Doppler shift frequency because the Doppler shift frequency and the blood velocity have the following relationship $$\Delta f = \frac{2 f_t v \cos\theta}{c}, \quad (1)$$

where $\Delta f$ is the Doppler shift frequency, $f_t$ is the transmitted frequency, $v$ is the blood velocity, $\theta$ is the angle between the ultrasound beam direction and the velocity vector, and $c$ is the speed of sound. The Doppler shift frequency is thus dependent on the angle between the velocity direction and the ultrasound beam direction and is a measurement that an ultrasound color Doppler system may obtain. Velocity (also called flow velocity, color velocity, color flow velocity, color Doppler velocity and others) derived from the Doppler shift frequency is usually the velocity component (i.e. $v \cos\theta$) in the ultrasound beam direction or the projection of true flow velocity $v$ onto to the ultrasound beam direction unless the angle is known or measured and corrected accordingly.

In the case of color Doppler, the number of the sampled signals may be limited to 10. Therefore, an auto-correlation technique is usually used to determine the phase differences between the wall-filtered I-Q signal and then to determine the Doppler shift frequency and the blood flow velocity as follows. The color Doppler's I-Q signals $z(n)=x(n)+jy(n)$ are used to calculate "auto-correlation" R as shown in the following equation, where $z(n)$ is the wall-filtered complex I-Q Doppler signal, $x(n)$ is the in-phase (real) signal, $y(n)$ is the quadrature phase (imaginary) signal, n indicates the signal number, j is the imaginary unit and * indicates the complex conjugate.

$$R = \Sigma z(n) \cdot z^*(n-1) \quad (2)$$

The real (Real(R)) and imaginary (Imag (R)) parts of R are used to obtain the phase $\phi$ as shown in the following equation.

$$\varphi = \tan^{-1} \frac{Imag(R)}{Real(R)} \quad (3)$$

Since $\tan^{-1}$ usually provides only $-0.5\pi$ to $0.5\pi$, the position of complex value R in the complex coordinate may be also used to derive $\phi$ in the range of $-\pi$ to $\pi$. The phase (i.e., color Doppler phase) $\phi$ is then related to the Doppler shift frequency as shown in the following equation.

$$\Delta f = \frac{\varphi f_{PRF}}{2\pi} \quad (4)$$

As shown in equation 4, a color Doppler phase of $2\pi$ corresponds to a Doppler shift frequency of the pulse repetition frequency $f_{PRF}$. Or a color Doppler phase of $\pi$ corresponds to a Doppler shift frequency of $$\frac{1}{2} f_{PRF}$$

while a color Doppler phase of $-\pi$ corresponds to a Doppler shift frequency of $$-\frac{1}{2} f_{PRF}.$$

A flow velocity (color flow velocity) in the positive direction corresponds to a positive Doppler shift frequency and a positive color Doppler phase while a flow velocity (color flow velocity) in the negative direction corresponds to a negative Doppler shift frequency and a negative color Doppler phase. Other techniques can be used to obtain the phase and the Doppler shift frequency and the blood flow velocity. The Doppler shift frequency indicates the blood flow velocity. Additionally, the power of the high-pass filtered Doppler I-Q signals indicates the existence of blood flow and the variance of the data indicates turbulence.

Because the color Doppler signals are obtained by the pulsed ultrasound (and also sampling) technique, sampling theory dictates a maximum frequency limit. The maximum frequency is generally half of the pulse repetition frequency (PRF) or $f_{PRF}$. Since the autocorrelation is performed on the complex I-Q Doppler signals, blood flow velocity in a negative direction appears in the negative frequency domain. Therefore, the color Doppler frequency includes negative frequencies that correspond to negative velocities (i.e., velocities having a direction away from the ultrasound transducer). For example, the Doppler shift frequency usually has a range of $$-\frac{f_{PRF}}{2}$$

to $$\frac{f_{PRF}}{2},$$

which in turn corresponds to a range of negative and positive (i.e., velocities having a direction towards the ultrasound transducer) maximum velocities.

Some embodiments employ other Doppler shift frequency ranges. For example, the range may incorporate a "baseline shift" in which the center frequency of the range is not equal to zero. In some embodiments, the baseline shift may be selected from a range of frequencies between $$-\frac{f_{PRF}}{2}$$

and $$\frac{f_{PRF}}{2}.$$

Figures 8A, 8B, 8C:
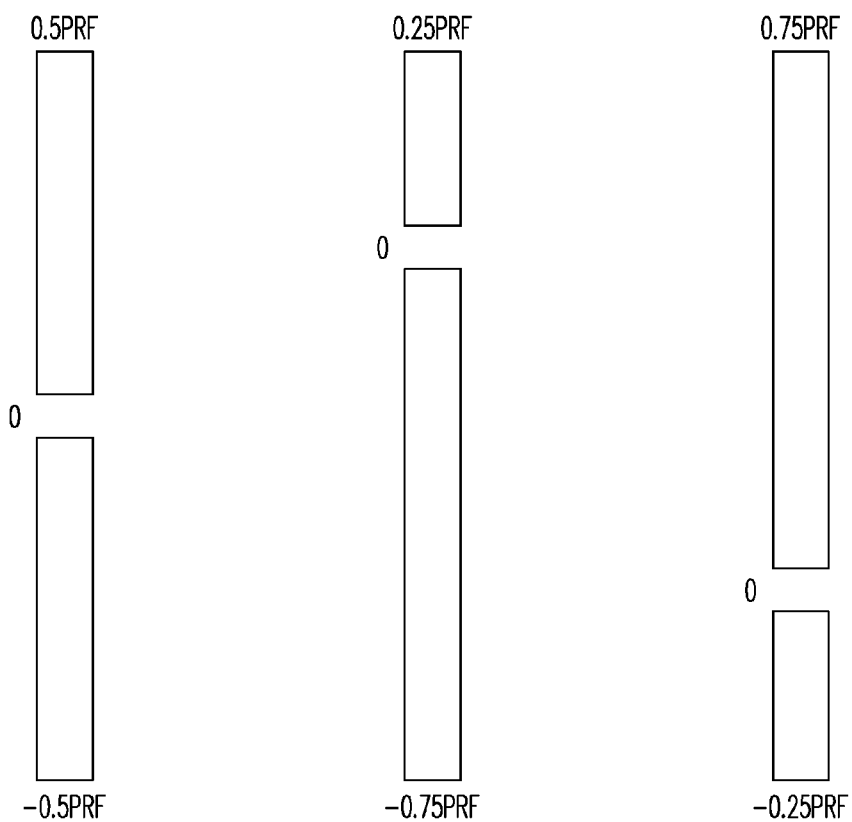
FIG. 8A: Color-coded Doppler shift frequency (velocity) scale with no baseline shift.
FIG. 8B: Color-coded Doppler shift frequency (velocity) scale with a baseline shift of $$\frac{f_{PRF}}{4}.$$
FIG. 8C: Color-coded Doppler shift frequency (velocity) scale with a baseline shift of $$-\frac{f_{PRF}}{4}.$$

In a particular example as shown in FIG. 8C, a Doppler shift frequency range of $$-\frac{f_{PRF}}{4}$$

to $$\frac{3f_{PRF}}{4}$$

reflects a baseline shift of $$-\frac{f_{PRF}}{4}.$$

This Doppler frequency range is associated with a negative maximum velocity corresponding to $$-\frac{f_{PRF}}{4}$$

and a positive maximum velocity corresponding to $$\frac{3f_{PRF}}{4}.$$

Similarly, a Doppler shift frequency range of $$-\frac{3f_{PRF}}{4}$$

to $$\frac{f_{PRF}}{4}$$

reflects a baseline shift of $$\frac{f_{PRF}}{4}$$

as shown in FIG. 8B. This Doppler frequency range is associated with a negative maximum velocity corresponding to $$-\frac{3f_{PRF}}{4}$$

and a positive maximum velocity corresponding to $$\frac{f_{PRF}}{4}.$$

In FIG. 8A, the baseline (i.e., 0 Hz) is in the center of the Doppler shift frequency (velocity) scale. When the baseline is shifted, e.g. by $$\frac{f_{PRF}}{4}$$

as shown in FIG. 8B, the positive maximum frequency becomes while the negative maximum frequency becomes $$-\frac{3f_{PRF}}{4}.$$

If the baseline shift is $$-\frac{f_{PRF}}{4},$$

the positive maximum frequency becomes $$\frac{3f_{PRF}}{4}$$

while the negative maximum frequency decreases to $$-\frac{f_{PRF}}{4}$$

as shown in FIG. 8C. In other words, the positive maximum frequency is decreased by the baseline shift while the absolute magnitude of the negative maximum frequency is increased by the baseline shift.

Often in cardiovascular applications, as well as in other applications, blood velocities may exceed these maximum velocities, resulting in aliasing. Color Doppler imaging uses color coding methods to display blood velocities (or corresponding Doppler shift frequencies) in colors. With respect to FIG. 1A, the positive velocities may be displayed in shades of red, with higher positive velocities represented by lighter red and lower positive velocities represented by darker red, while the negative velocities may be displayed in shades of blue, with higher negative velocities represented by lighter blue and lower negative velocities represented by darker blue as shown in the color coding bars in the left hand side of FIG. 1A. The positive maximum velocity is represented by light red color 102 while the negative maximum velocity is represented by light blue color 110. The positive minimum velocity is represented by dark red color 104 while the negative minimum velocity is represented by dark blue color 108. Black 106 represents zero velocity. Other color coding methods can be used to represent blood flow velocities.

Figure 1A:
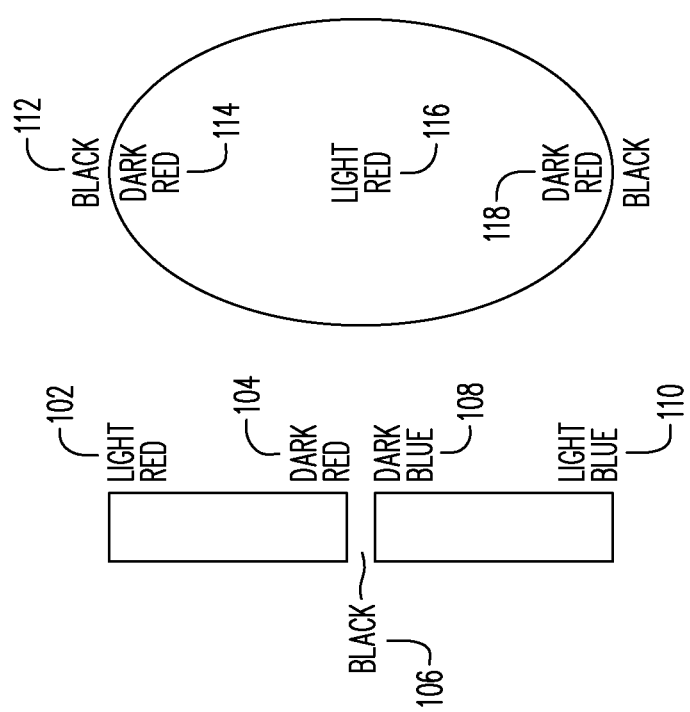
FIG. 1A: Color Doppler image.

A color flow image in the right hand side of FIG. 1A includes shades of red including light red 116 in the center and dark red 114, 118 at the top and bottom and apparently is not aliased.

When aliasing occurs, the color flow image may "wrap around" at velocities corresponding to the positive maximum frequency, with velocities corresponding to frequencies which exceed the positive maximum frequency represented by colors associated with negative velocities (e.g., shades of blue). Conversely, aliasing may cause velocities corresponding to frequencies which exceed (in absolute value) the negative maximum frequency to be represented by colors associated with positive velocities (e.g., shades of red). Aliasing therefore complicates the blood velocity image and makes any diagnosis based thereon difficult. FIG. 1B, for example, shows a color flow image which most likely exhibits aliasing. The center area is colored by shades of blue 166 and surrounded by an area of shades of red 164 which is in turn surrounded by areas of black 162. In this case, the center flow area of shades of blue 166 is most likely aliased.

Figure 11:
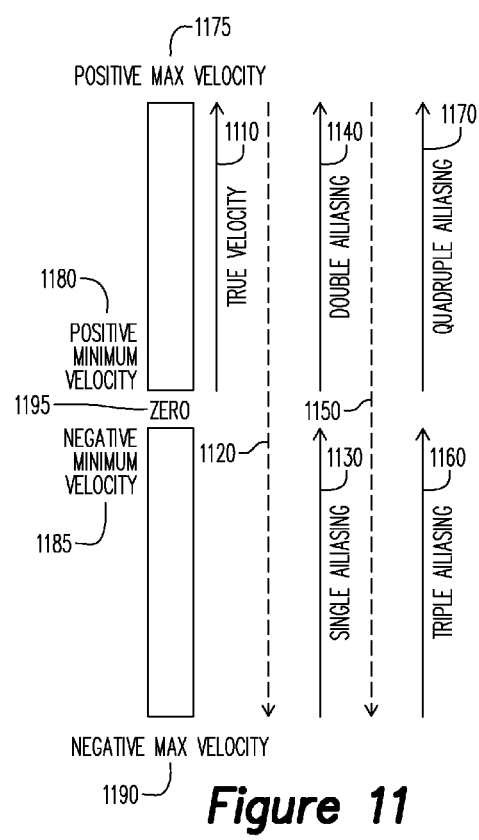
FIG. 11: Diagram of velocity aliasing of various degrees in the positive velocity direction.
Figure 12:
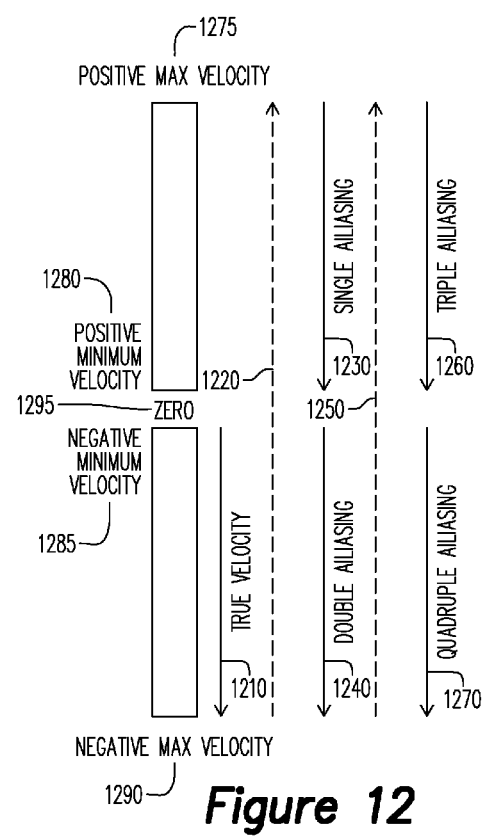
FIG. 12: Diagram of velocity aliasing of various degrees in the negative velocity direction.

Flow velocities may "wrap around" at the velocity limits (maximum velocity magnitude) more than once, in that they exceed the maximum velocity and the minimum velocity of the opposite velocity direction. FIGS. 11 and 12 illustrate such "double-aliasing", "triple-aliasing" and "quadruple-aliasing", in addition to the previously-described "single-aliasing". For example, positive velocities may exceed the positive maximum velocity 1175 and wrap around to the negative maximum velocity 1190 as shown by the dotted arrow 1120. The velocity range 1110 shows a true velocity range 1110. Once the aliasing occurs, the velocity range becomes "single-aliased" velocity range 1130 as shown in FIG. 11. The velocity then may further exceed zero velocity 1195 (or the negative minimum velocity 1185) and change the velocity direction again, resulting in positive velocities which may be called "double-aliased" velocities 1140. Then the velocity may further exceed the positive maximum velocity 1175 again and wrap around to the negative maximum velocity 1190 as shown by the dotted arrow 1150. The velocity may further increase in the "triple-aliased" velocity range 1160. The velocity then may further increase and go across the zero velocity 1195 and change the velocity direction, resulting in the positive velocities which may be called "quadruple aliased" velocities 1170. The above discussion of aliasing, "single-aliasing", "double-aliasing", "triple-aliasing", and "quadruple-aliasing" may also apply to the opposite direction as shown in FIG. 12.

For such aliasing, aliasing correction may include adding $V_{PRF}$ to the velocities of a "double-aliased" flow area if the "double-aliased" velocity is positive. If the double-aliased velocity is negative, $V_{PRF}$ is subtracted from the velocities. Similarly, for a "triple aliased" flow area, $2V_{PRF}$ is subtracted from the triple-aliased velocities if the velocities are positive, and $2V_{PRF}$ is added to the triple-aliased velocities if the velocities are negative. For a "quadruple-aliased" flow area, $2V_{PRF}$ is added to the velocities if the velocities are positive, and $2V_{PRF}$ is subtracted from velocities if the velocities are negative.

Figure 9B:
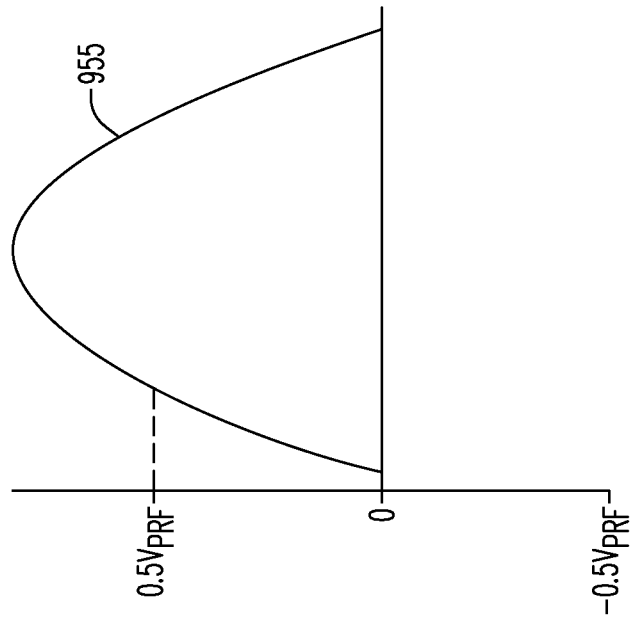
FIG. 9B: Color Doppler velocity distribution across a vessel with aliasing correction.
Figure 9A:
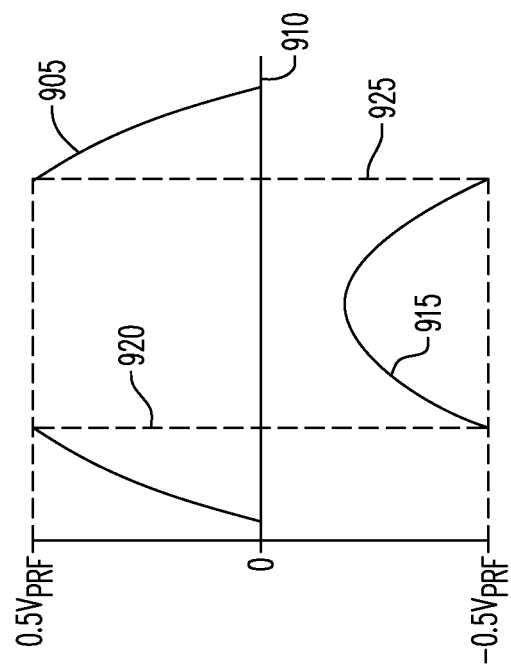
FIG. 9A: Color Doppler velocity distribution across a vessel with aliasing.

Flow or blood flow must follow physics or fluid mechanics laws. For example, flow velocity cannot change too rapidly spatial-wise, meaning velocity gradients or differences cannot be too large. FIG. 9A shows an example of velocities 905 measured by color Doppler techniques. The horizontal axis is a spatial coordinate 910 (for example, a vessel diameter) and the vertical axis represents the color Doppler velocity. At the left spatial point, the velocity 905 is virtually zero (0) and then increases gradually as the spatial point moves to the right until the velocity 905 reaches $0.5V_{PRF}$ and then suddenly changes to $-0.5V_{PRF}$. Then, the velocity 915 increases from $-0.5V_{PRF}$ to approximately $-0.2V_{PRF}$ and then decreases back to $-0.5V_{PRF}$. When the velocity 915 reaches $-0.5V_{PRF}$, it suddenly jumps back to $0.5V_{PRF}$.

FIG. 9A therefore represents a typical example of aliasing. At the transitions 920, 925, from $0.5V_{PRF}$ to $-0.5V_{PRF}$ and from $-0.5V_{PRF}$ to $0.5V_{PRF}$, the velocity differences are very large. If velocity is spatially continuously sampled, the velocity difference across the transition is $V_{PRF}$. The negative velocities 915 in FIG. 9A are all aliased. If this aliasing is corrected, the correct velocity distribution (profile) 955 may be obtained as shown in FIG. 9B. The velocity difference across the old transition is very small after aliasing correction, and may approach zero. FIGS. 9A and 9B show velocity distributions in one-dimension for simplicity.

Figure 13:
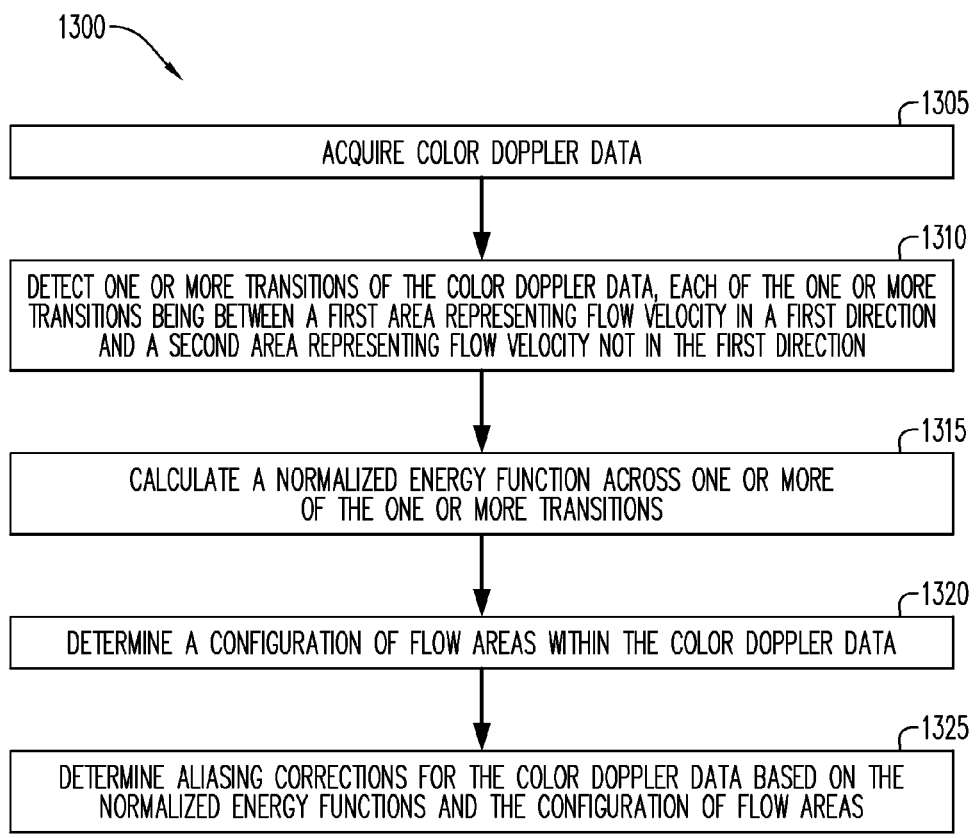
FIG. 13: A flow diagram of a process to address aliasing correction according to some embodiments.

FIG. 13 is a flow diagram of process 1300 according to some embodiments. Process 1300 may be performed by any combination of hardware and/or software that is or becomes known. For example, process 1300 may be embodied in processor-executable program code stored on a non-transitory medium (e.g., Digital Video Disc, computer hard drive, Random Access Memory, etc.).

Initially, at 1305, color Doppler data including color flow lines or color Doppler images are acquired. One or more transitions in the color Doppler data are then detected at 1310. The one or more transitions may include transitions between a positive flow velocity area and a negative flow velocity area, between a negative flow velocity area and a zero flow velocity area, and/or between a positive flow velocity area and a zero flow velocity area.

Next, at 1315, a normalized energy function across one or more of the one or more transitions is calculated. As will be described in detail below, the normalized energy function may be based on one or more pairs of flow velocities (or color Doppler values, i.e., the Doppler shift frequency or the color Doppler phase) located on opposite sides of the transition.

A normalized energy function according to some embodiments is as follows:

$$\frac{1}{n}\sum_{i=1}^{n}|V_{1i}-V_{2i}|, \quad (5)$$

where n is the number of velocity pairs across the transition, $V_{1i}$ represents a velocity on one side of the transition while $V_{2i}$ represents a velocity on the other side of the transition for example as shown in FIG. 2A.

The normalized energy function (5) may yield an absolute mean of velocity differences across a transition, which may be considered as a measure of a magnitude of the transition. The mean of velocity differences may be compared with a standard to determine whether the transition may involve aliasing. For example, if the normalized energy function is greater than a threshold, the transition may be assumed to involve aliasing. In some embodiments, the threshold is equal to $0.5V_{PRF}$.

With reference to FIG. 2A, flow velocities (e.g., $V_{11}$, $V_{12}$, ...) are obtained by color Doppler near a transition 218 from shades of red 214 (positive velocities) to shades of blue 216 (negative velocities). $V_{11}, V_{12}, \ldots V_{1i}$ are on the blue color side of the transition and are sampled at an equal spatial distance while $V_{21}, V_{22}, \ldots V_{2i}$ are on the red side of the transition and sampled at an equal spatial distance. $V_{1i}$ and $V_{2i}$ may be very close to each other across the transition 218, where i may be between 1 and n. In some embodiments, velocities are sampled at unequal spatial distances.

The normalized energy function (5) across the transition is then calculated. Some embodiments of 1315 calculate a normalized energy function based on normalized power function (6) or the normalized sum of the p-th power of the absolute differences of velocities (7).

$$\frac{1}{n}\sum_{i=1}^{n}(V_{1i}-V_{2i})^2 \text{ or} \quad (6)$$

$$\frac{1}{n}\sum_{i=1}^{n}|V_{1i}-V_{2i}|^p \quad (7)$$

Flow velocities (i.e., $V_{31}, V_{32}, \ldots V_{3i}$) are also obtained near the transition from red colors (positive velocities) to black (zero velocities). Since the velocities associated with the black area are zero, a normalized energy function may be obtained as follows, $$\frac{1}{n2}\sum_{i=1}^{n2}|V_{3i}|, \quad (8)$$

where n2 is the number of velocity samples.

A more complicated case is shown in FIG. 2B. In this example, the center area includes shades of red 268, indicating positive velocities, and is surrounded by a ring-like area of shades of blue 266, which in turn is surrounded by another ring-like area of shades of red 264, which is surrounded by black areas 262. Therefore, FIG. 2B illustrates three transitions 270, 272, 274. Velocities on one side of the first transition 270 are marked by $V_{11}, V_{12}, \ldots, V_{1i} \ldots$, while corresponding velocities on the other side of the first transition 270 are marked by $V_{21}, V_{22}, \ldots, V_{2i}, \ldots$. A normalized energy function across the first transition 270 is obtained at 1315 as follows, $$\frac{1}{n}\sum_{i=1}^{n}|V_{1i}-V_{2i}|, \quad (9)$$

where n is the number of velocity samples.

Velocities on the blue-shaded side of the second transition 272 are marked by $V_{31}, V_{32}, \ldots, V_{3i}, \ldots$, while the corresponding velocities of the red-shaded side of the second transition 272 are marked by $V_{41}, V_{42}, \ldots V_{4i} \ldots$. A normalized energy function across the second transition 272 is obtained as follows, $$\frac{1}{n2}\sum_{i=1}^{n2}|V_{3i}-V_{4i}|, \quad (10)$$

where n2 is the number of velocity samples.

Velocities on the red-shaded side of the third transition 274 are marked by $V_{51}, V_{52}, \ldots V_{5i}, \ldots$, while the black areas 262 represent zero velocities. A corresponding normalized energy function for the third transition 274 is therefore obtained as follows, $$\frac{1}{n3}\sum_{i=1}^{n3}|V_{5i}|, \quad (11)$$

where n3 is the number of velocity samples.

According to some embodiments, the number of flow velocities on each side of the transition need not be identical. Consequently, a same flow velocity on a side of the transition may belong to more than one of the one or more pairs of flow velocities in the normalized energy function. For example, with respect to FIG. 2B, calculation of a normalized energy function at 1315 may include determination of an absolute difference between flow velocity pair ($V_{31}$, $V_{41}$) and of an absolute difference between flow velocity pair ($V_{31}$, $V_{42}$).

Figure 10:
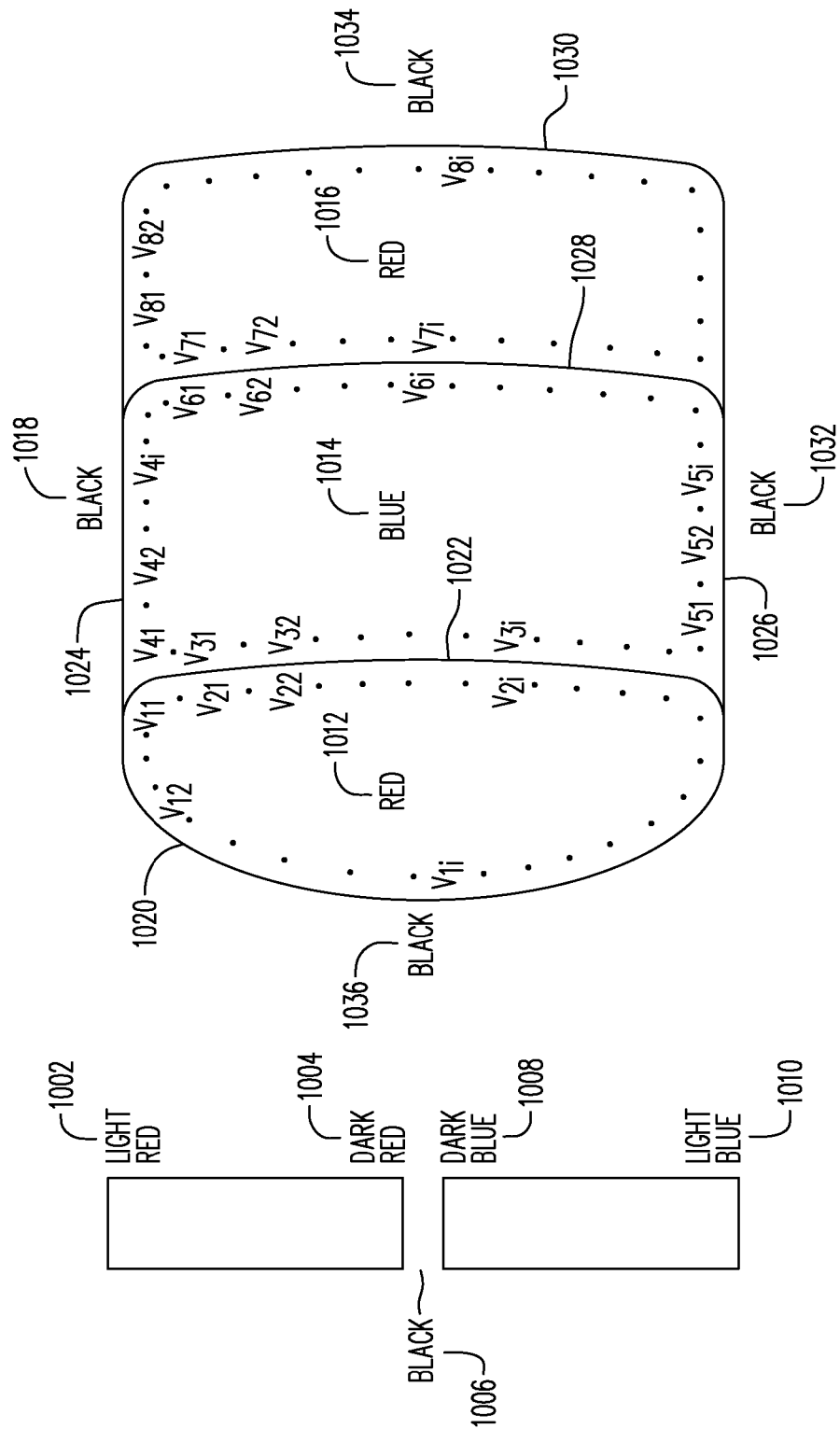
FIG. 10: Color Doppler image with three flow areas.

FIG. 10 illustrates a color flow image in which flow areas are divided into three areas of red shades 1012, blue shades 1014 and red shades 1016. The image includes a first transition 1020 between the black area 1036 (i.e., zero velocity) and the left-most red-shaded area 1012. Velocities adjacent to this transition are marked by $V_{11}, V_{12}, \ldots, V_{1i}, \ldots$ while the black area 1036 may have zero velocities. For this transition 1020, a normalized energy function may be obtained as follows, $$\frac{1}{n}\sum_{i=1}^{n}|V_{1i}|, \qquad (12)$$

where n is the number of velocity samples.

The second transition 1022 is between the left-most red-shaded area 1012 and the blue-shaded area 1014. Velocities on the red-shaded side of the transition 1022 are marked by $V_{21}, V_{22}, V_{2i}, \ldots$, while the corresponding velocities on the blue-shaded side of the transition 1022 are marked by $V_{31}, V_{32}, V_{3i}, \ldots$. For this transition 1022, a normalized energy function may be obtained as follows, $$\frac{1}{n2}\sum_{i=1}^{n2}|V_{2i} - V_{3i}|, \qquad (13)$$

where n2 is the number of velocity samples.

A third transition 1024 exists between the blue-shaded area 1014 and a black area 1018 at the top of the color flow image. Velocities on the blue-shaded side of the transition 1024 are marked by $V_{41}, V_{42}, \ldots, V_{4i}, \ldots$ while the black area may have zero velocities. For this transition 1024, a normalized energy function may be obtained as follows, $$\frac{1}{n3}\sum_{i=1}^{n3}|V_{4i}|, \qquad (14)$$

where n3 is the number of velocity samples.

The fourth transition 1026 is between the blue-shaded area 1014 and a black area 1032 at the bottom of the color flow image. Velocities on the blue-shaded side of the transition 1026 are marked by $V_{51}, V_{52}, \ldots, V_{5i}, \ldots$ while the black area 1032 may have zero velocities. For this transition 1026, a normalized energy function may be obtained as follows, $$\frac{1}{n4}\sum_{i=1}^{n4}|V_{5i}|, \qquad (15)$$

where n4 is the number of velocity samples.

A fifth transition 1028 exists between the blue-shaded area 1014 and the right-most red-shaded area 1016. Velocities on the blue-shaded side of the transition 1028 are marked by $V_{61}, V_{62}, \ldots, V_{6i} \ldots$ while velocities on the red-shaded side of the transition 1028 are marked by $V_{71}, V_{72}, \ldots, V_{7i}, \ldots$. For this transition 1028, a normalized energy function may be obtained as follows, $$\frac{1}{n5}\sum_{i=1}^{n5}|V_{6i} - V_{7i}|, \qquad (16)$$

where n5 is the number of velocity samples.

The sixth transition 1030 is between the right-most red-shaded area 1016 and the black area 1034. Velocities on the red-shaded side of the transition 1030 are marked by $V_{81}, V_{82}, \ldots, V_{8i} \ldots$ while the black area 1034 may have zero velocities. For this transition 1030, a normalized energy function may be calculated at 1315 as follows, $$\frac{1}{n6}\sum_{i=1}^{n6}|V_{8i}|, \qquad (25)$$

where n6 is the number of velocity samples.

Returning to process 1300, a configuration of flow areas within the color Doppler data is determined at 1320. The configuration represents the physical (geometrical?) relationships between various flow areas in the color Doppler data. 1320 may therefore include determining, for each flow area, whether the flow area is in contact with a zero velocity area, and whether the flow area is surrounded by and in contact with a flow area of opposite velocity direction.

Figure 18:
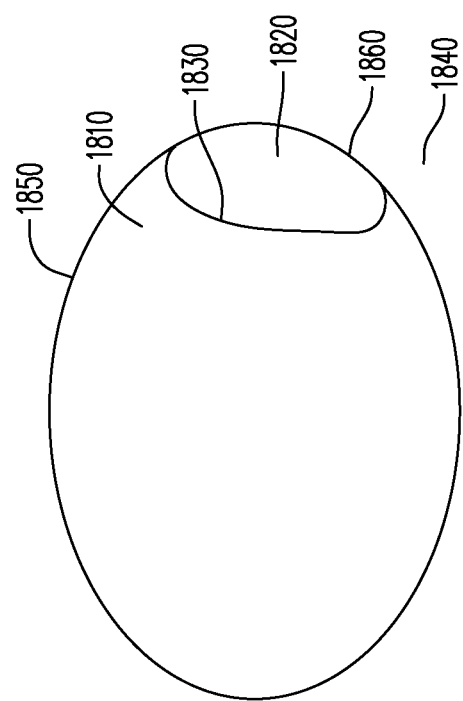
FIG. 18. Color Doppler image including two flow areas.

For example, FIG. 18 illustrates a flow area 1810 of a first flow direction, a flow area 1820 of a second flow direction, and a transition 1830 between the flow areas 1810, 1820. Both flow areas 1810, 1820 are surrounded by a zero velocity area 1840.

Figure 15:
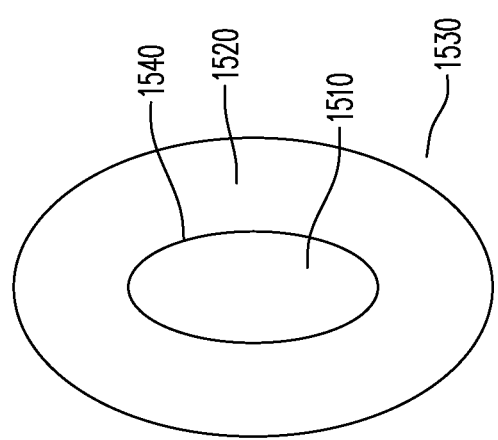
FIG. 15. Color Doppler image including a single-inclusion.

FIG. 15 illustrates an inclusion, which generally refers to a flow area surrounded by and in contact with a flow area of opposite velocity direction. In FIG. 15, a first flow area 1510 of a first flow direction is surrounded by a second flow area 1520 of a second (and opposite) flow direction which is in contact with an area 1530 of zero velocities. A transition 1540 exists between the first flow area 1510 and the second flow area 1520.

Flow area 1510 is considered a single inclusion because flow area 1520 is not surrounded by and in contact with a flow area of opposite velocity direction. In contrast, FIGS. 16 and 17 illustrate double and triple inclusions, respectively.

Figure 16:
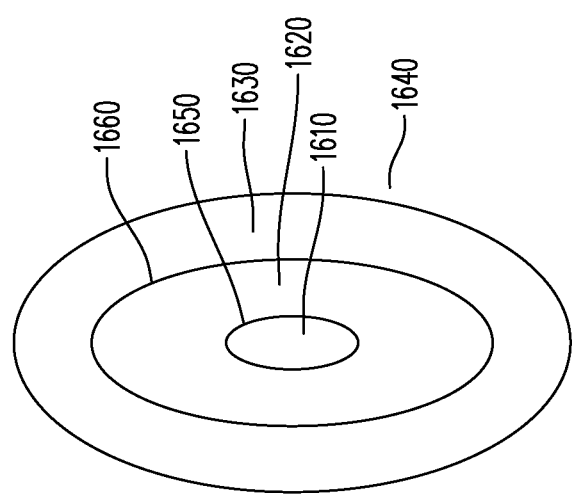
FIG. 16. Color Doppler image including a double-inclusion.

FIG. 16 shows a first (double inclusion) flow area 1610 of a first flow direction surrounded by and in contact with a second (single inclusion) flow area 1620 of a second (and opposite) flow direction which is in turn surrounded by and in contact with a third flow area 1630 of the first flow direction. Flow area 1630 is surrounded by and in contact with an area 1640 of zero velocities. A transition 1650 exists between the first flow area 1610 and the second flow area 1620. Another transition 1660 exists between the second flow area 1620 and the third flow area 1630.

Figure 17:
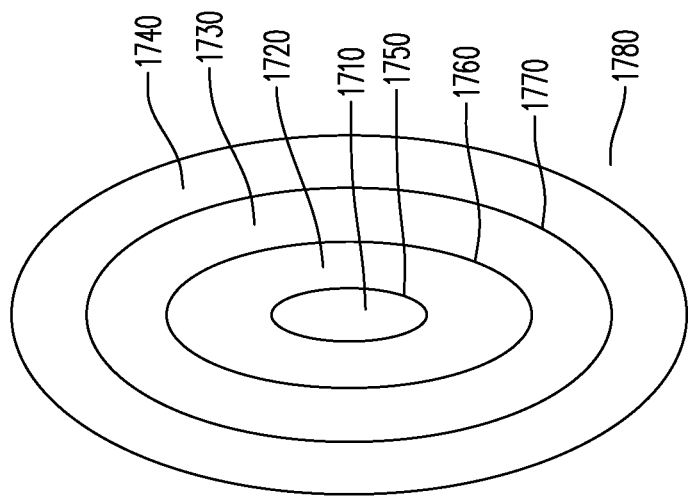
FIG. 17. Color Doppler image including a triple-inclusion.

Turning to FIG. 17, a first (triple inclusion) flow area 1710 of a first flow direction is surrounded by a second (double inclusion) flow area 1720 of a second (and opposite) direction, which is surrounded by and in contact with a third flow area 1730 of the first flow direction, which in turn is surrounded by and in contact with a fourth flow area 1740 of the second flow direction. Flow area 1740 is surrounded by and in contact with an area 1780 of zero velocities. A first transition 1750 exists between the first flow area 1710 and the second flow area 1720. A second transition 1760 exists between the second flow area 1720 and the third flow area 1730. A third transition 1770 exists between the third flow area 1730 and the fourth flow area 1740.

After determining the configuration of the flow areas, aliasing corrections for the color Doppler data are determined at 1325. Determination of the aliasing corrections is based on the normalized energy functions and the configuration of the flow areas.

One or more of the following general principles may be adopted in some embodiments to guide the determination of aliasing corrections at 1325:

a) No aliasing may be initially assumed if the normalized energy function across each transition is less than a threshold (e.g., $V_{PRF}$).

b) Single-aliasing may be initially assumed if the normalized energy function across a transition is greater than a threshold (e.g., $V_{PRF}$).

c) No aliasing may be initially assumed if a flow area is in contact with a zero velocity area. However, if the flow area is also adjacent to a transition whose normalized energy function is greater than the threshold, a total energy function may be calculated to determine which side of the transition is single-aliased. The total energy function is simply the sum total of the non-normalized energy functions of all transitions.

d) For an inclusion surrounded by a flow area of the opposite velocity direction which is, in turn, in contact with a zero velocity area (e.g., FIG. 2A), the inclusion may be considered single-aliased. This assumption may be supported if the normalized energy function across a transition surrounding the inclusion is greater than a threshold.

e) For a double inclusion which is surrounded by and in contact with a flow area of the opposite velocity direction (direction A), which in turn is surrounded by and in contact with another flow area of opposite direction (direction B), the double inclusion may be considered double-aliased. This assumption may be further supported if the normalized energy function across the transition adjacent to the double inclusion is less than the threshold. If the normalized energy function is greater than the threshold, the double inclusion area may be considered not aliased. However, a flow area adjacent to the double inclusion area may be considered single-aliased.

f) For a triple inclusion, a normalized energy function may be calculated for all transitions surrounding the triple inclusion to determine if each transition meets the conditions of an aliased transition associated with a certain degree of aliasing. In the case of a single-aliased transition, the normalized energy function may be greater than the threshold. A double-aliased transition may be associated with a normalized energy function less than the threshold. A triple-aliased transition may be associated with a normalized energy function greater than the threshold.

Furthermore, the location of the transition may determine the degree of aliasing. That is, a double-aliased transition may be disposed within a single-aliased transition and a triple-aliased transition may be disposed within the double-aliased transition if the normalized energy function of each transition meets the above-mentioned conditions. If the normalized energy function of a transition inside the double-aliased transition doesn't meet the conditions of the triple-aliased transition, the transition may be considered single-aliased and velocities of the center flow area may be considered single-aliased.

Examples of various aliasing correction determinations are now provided. According to the examples, one or more aliasing corrections may be determined for the color Doppler data.

With respect to FIG. 18, no aliasing correction may be determined for flow areas 1810, 1820 if the normalized energy function of one or more transitions (1830, 1850, 1860) is less than a preset threshold. The preset threshold may be a velocity corresponding to the Doppler shift frequency of half the pulse repetition frequency. In some embodiments, no aliasing may be determined for each flow area (1810 or 1820) that is in contact with zero velocity area 1840.

In some embodiments, single aliasing correction may be determined for one flow area 1820 or 1830 in contact with a transition 1830 if the normalized energy function across the transition 1830 is greater than the preset threshold.

In some embodiments, single aliasing correction may be determined for the flow area 1820 because it contacts the zero flow area 1840 and because a normalized energy function across transition 1830 with the opposite flow velocity area 1810 is greater than the preset threshold. Single aliasing correction is determined for the smaller flow area 1820 of the transition 1830, which is associated with a normalized energy function of greater than the preset threshold, because the area of the flow area 1820 is smaller than that of the flow area 1810 and because the likelihood of aliasing in the smaller flow area 1820 is higher than in the larger flow area 1810.

Alternatively, single aliasing correction may be performed on a flow area after calculating the total energy function with single aliasing correction applied on only one of the flow areas (1810 or 1820) and confirming that a total energy function calculated with single aliasing correction applied on only one of the flow areas (1810 or 1820) and no aliasing correction on the other flow area 1810 is smaller than a total energy function calculated with single aliasing correction applied on only one 1810 of the flow areas (1810 or 1820) and no aliasing correction on the flow area 1820.

Figure 14:
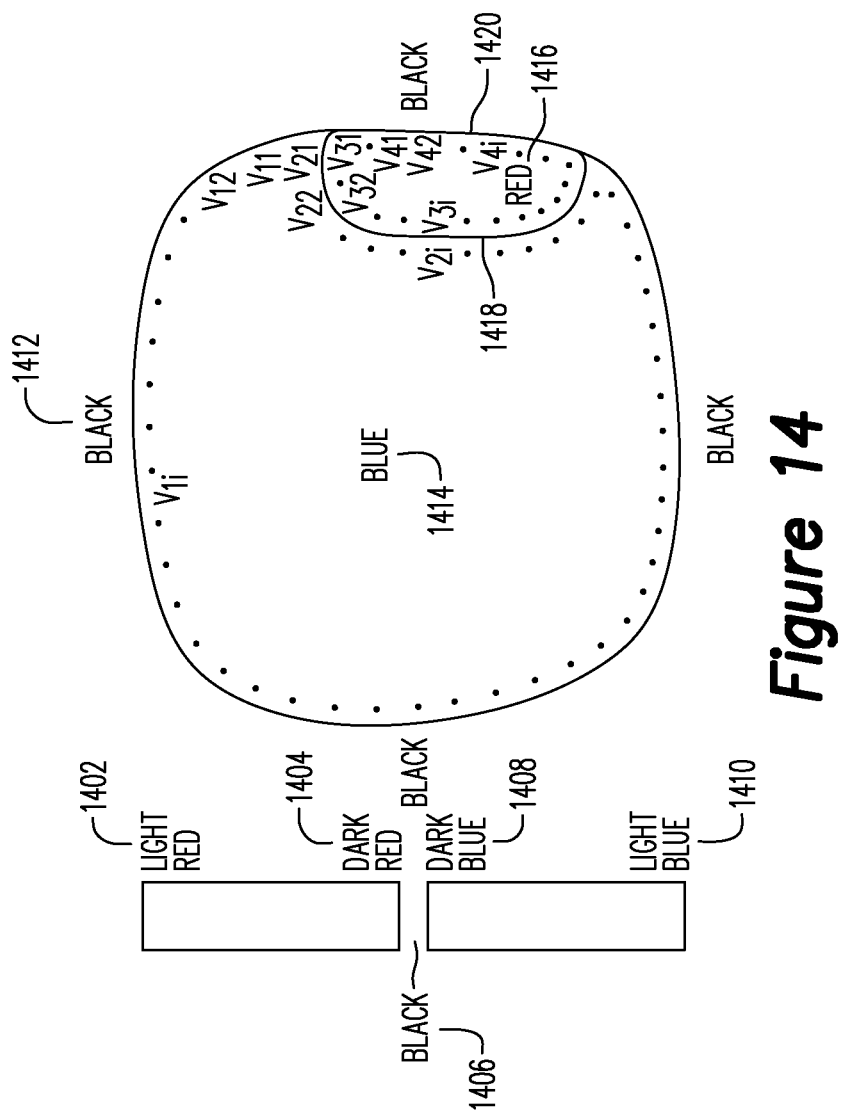
FIG. 14. Color Doppler image including two flow areas.

For a more specific example of the use of a total energy function, FIG. 14 illustrates an example of a color flow image including two color flow areas: a large blue flow area 1414 and a small red flow area 1416. Both color flow areas 1414, 1416 are adjacent to black areas 1412 representing velocities of zero. Generally, flow areas in contact with zero velocities may be initially considered to be non-aliased. However, the normalized energy function for a transition 1418 between the blue flow area 1414 and red flow area 1416 may be calculated as follows, $$\frac{1}{n2}\sum_{i=1}^{n2}|V_{2i} - V_{3i}|, \quad (26)$$

where n2 is the number of velocity samples. If the normalized energy function is greater than the threshold (e.g., $V_{PRF}$), aliasing (e.g., single-aliasing) may be assumed. That is, it is assumed that velocities of one of the two flow areas 1414, 1416 may be single-aliased. Since the red flow area 1416 is much smaller than the blue flow area 1414 and since the following total energy function (27) is smaller if it is assumed that the red flow area 1416 (and not the blue flow area) is aliased, the red flow area 1416 may be assumed to be single-aliased.

$$\sum_{i=1}^{n}|V_{1i}| + \sum_{i=1}^{n2}|V_{2i} - V_{3i}| + \sum_{i=1}^{n3}|V_{4i}|, \quad (27)$$

where n, n2, and n3 are the numbers of velocity samples at the three transitions.

In some embodiments, velocities are sampled at an equal distance, therefore the numbers indicate the length of the transitions. As a result, a longer transition carries more weight than a shorter transition. In other words, the blue flow area 1414 may exhibit a higher probability of being non-aliased than the smaller red area 1416. If single-aliasing correction is applied to velocities in the red flow area, the total energy function would be smaller than (27) as follows, $$\sum_{i=1}^{n} |V_{1i}| + \sum_{i=1}^{n2} |V_{2i} - (V_{3i} - V_{PRF})| + \sum_{i=1}^{n3} |V_{4i} - V_{PRF}|. \quad (28)$$

(28) would be smaller than (27), and also smaller than the following total energy function (29), which assumes that the blue flow area is aliased because of the above-mentioned weight.

$$\sum_{i=1}^{n} |V_{1i} + V_{PRF}| + \sum_{i=1}^{n2} |(V_{2i} + V_{PRF}) - V_{3i}| + \sum_{i=1}^{n3} |V_{4i}| \quad (29)$$

Accordingly, it may only be necessary to calculate the normalized energy function (26) in order to determine aliasing corrections for the color Doppler data of FIG. 14. Calculation of total energy function (29) is not required, and total energy function (28) may be calculated and compared with total energy function (27) for confirmation of the conclusion reached via normalized energy function (26). In this case, since a transition between the blue flow area and the red flow area is longer than a transition between the red flow area and the black area, total energy function (28), which assumes single-aliasing in the red flow area, may be smaller than total energy function (27), which assumes no aliasing in any flow area. Embodiments may therefore provide fast and efficient aliasing correction.

Now referring to FIG. 15, single aliasing correction may be determined for the first flow area (single inclusion) 1510 and no aliasing correction may be determined for the second flow area 1520 in some embodiments based on the above-described general principles. In some embodiments, single aliasing correction may be determined for the first flow (single inclusion) area 1520 and no aliasing correction may be determined for the second flow area 1520 if the normalized energy function of the transition 1540 is greater than a preset threshold.

In FIG. 16, and based on above principles d) and e), double aliasing correction may be determined for the first (double-inclusion) flow area 1610, single aliasing correction may be determined for the second flow area 1620, and no aliasing correction may be determined for the third flow area 1630.

In some embodiments, double aliasing correction may be determined for the first (double-inclusion) flow area 1610, single aliasing correction may be determined for the second (single inclusion) flow area, and no aliasing correction may be determined in the third flow area only if the normalized energy function across the double-inclusion's transition 1650 is less than a preset threshold and if the normalized energy function across the single inclusion's transition 1660 is greater than a preset value.

According to some embodiments, no aliasing correction may be determined for the first flow (double-inclusion) area 1610, single aliasing correction may be determined for the second (single inclusion) flow area 1620 and no aliasing correction may be determined for the third flow area 1630 if the normalized energy function across the double-inclusion's transition 1650 is greater than the preset threshold value, and if the normalized energy function across the single inclusion's transition 1660 is greater than the preset value.

In some embodiments, single aliasing correction may be determined for the second flow (single-inclusion) area 1620 and no aliasing correction may be determined for the third flow area 1630 if the normalized energy function across the single inclusion's transition 1660 is greater than the preset threshold.

Cases of triple-inclusions such as FIG. 17 may provide even greater alternatives for determining aliasing corrections. For example, triple aliasing correction may be determined for the first (triple-inclusion) flow area 1710, double aliasing correction may be determined for the second (double inclusion) flow area 1720, single aliasing correction may be determined for the third (single inclusion) flow area 1730, and no aliasing correction may be determined for the fourth flow area 1740.

In some embodiments, triple aliasing correction may be determined for the first (triple-inclusion) flow area 1710, double aliasing correction may be determined for the second (double-inclusion) flow area 1720, single aliasing correction may be determined for the third (single inclusion) flow area 1730 and no aliasing correction may be determined for the fourth area 1740 if the normalized energy function across the first (triple-inclusion's) transition 1750 is greater than a preset threshold, if the normalized energy function across the second (double inclusion's) transition 1760 is less than the preset threshold, and if the normalized energy function across the third (single inclusion's) transition 1770 is greater than the preset threshold.

In some embodiments, single aliasing correction may be determined for the first (triple-inclusion) flow area 1710, double aliasing correction may be determined for the second (double inclusion) flow area 1720, single aliasing correction may be determined for the third (single inclusion) flow area 1730, and no aliasing correction may be determined for the fourth flow area 1740 if the normalized energy function across the first (triple-inclusion's) transition 1750 is less than the preset threshold, if the normalized energy function across the second (double inclusion's) transition 1760 is less than the preset threshold, and if the normalized energy function across the third (single inclusion's) transition 1770 is greater than the preset threshold.

In some embodiments, double aliasing correction may be determined for the second (double inclusion) flow area 1720, single aliasing correction may be determined for the third (single inclusion) flow area 1730, and no aliasing correction may be determined for the fourth flow area 1740 if the normalized energy function of the second (double inclusion's) transition 1760 is less than the preset threshold and if the normalized energy function of the third (single inclusion's) transition 1770 is greater than the preset threshold.

In some embodiments, no aliasing correction may be determined for the second (double inclusion) flow area 1720, single aliasing correction may be determined for the third (single inclusion) flow area 1730 and no aliasing may be determined for the fourth flow area 1740 if the normalized energy function across the second (double inclusion's) transition 1760 is greater than the preset threshold and if the normalized energy function across the third (single inclusion's) transition 1770 is greater than the preset threshold.

In some embodiments, single aliasing correction may be determined for the third (single inclusion) flow area 1730 and no aliasing correction may be determined for the fourth flow area 1740 if the normalized energy function across the third (single inclusion's) transition 1770 is greater than the preset threshold.

In some embodiments, no aliasing correction may be determined for the third (single inclusion) flow area 1730 if the normalized energy function across the third (single inclusion's) transition 1770 is less than the preset threshold.

In some embodiments, no aliasing correction may be determined for the fourth flow area 1740 which is surrounded by the zero velocity area 1780.

After performance of process 1300, some embodiments then apply the determined aliasing corrections (if any) to the flow areas of the color Doppler data. All velocities of a same continuous flow area of a same velocity direction are corrected the same way, i.e., if $V_{PRF}$ is added to a velocity of a flow area, $V_{PRF}$ is added to all other velocities in the same flow area.

Figure 6B:
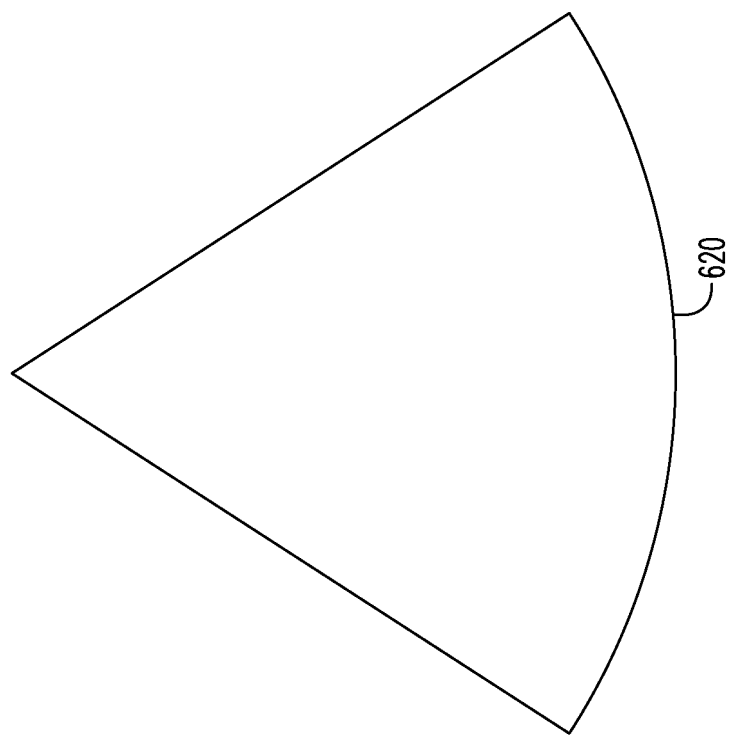
FIG. 6B: A representation of a scan-converted color flow image.
Figure 6A:
FIG. 6A: A representation of color flow lines.
Figure 7B:
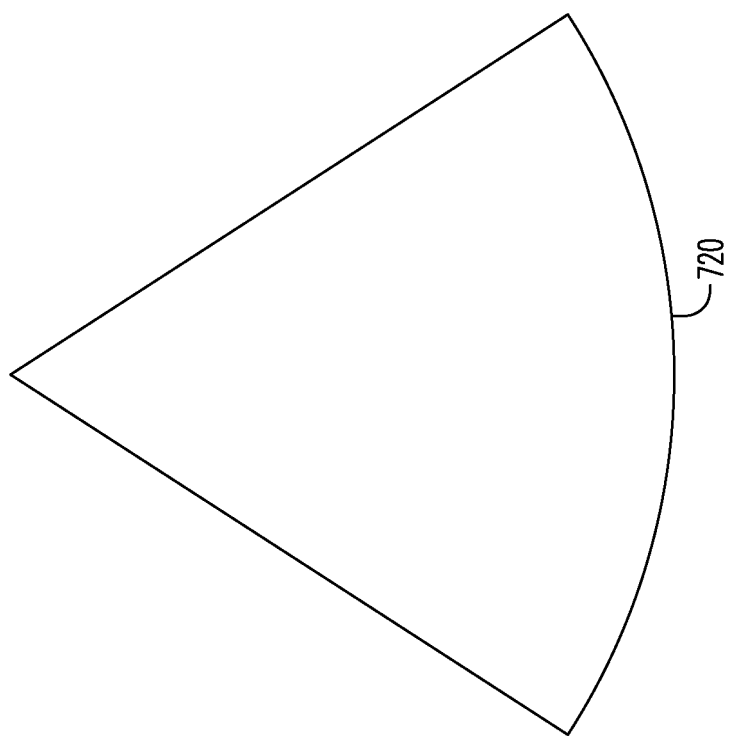
FIG. 7B: A representation of a scan-converted B-mode image.
Figure 7A:
FIG. 7A: A representation of B-mode lines.

As mentioned above, the method may be applied to color flow line data or color Doppler image data according to some embodiments. FIG. 6A shows color flow lines 600 before scan-conversion, although only 11 lines are shown as an example. A color flow line consists of many color flow data samples along the line. Color flow lines 600 are created from color beam data and may not show correct spatial dimensions. Scan-conversion is a technique to convert the color flow lines to a raster video image by interpolating the color flow lines. In a scan-converted image 620 (e.g., sector scan) shown FIG. 6B, the color flow image consists of color flow image pixels of the orthogonal (x-y) coordinate with the correct length relationship (vertical vs. horizontal dimensions) in contrast to the color flow lines 600 shown in FIG. 6A. B-mode imaging also uses the scan-conversion technique to convert B-mode lines 700 as shown in FIG. 7A to a B-mode image 720 as shown in FIG. 7B by interpolating B-mode line data 700.

Figure 3:
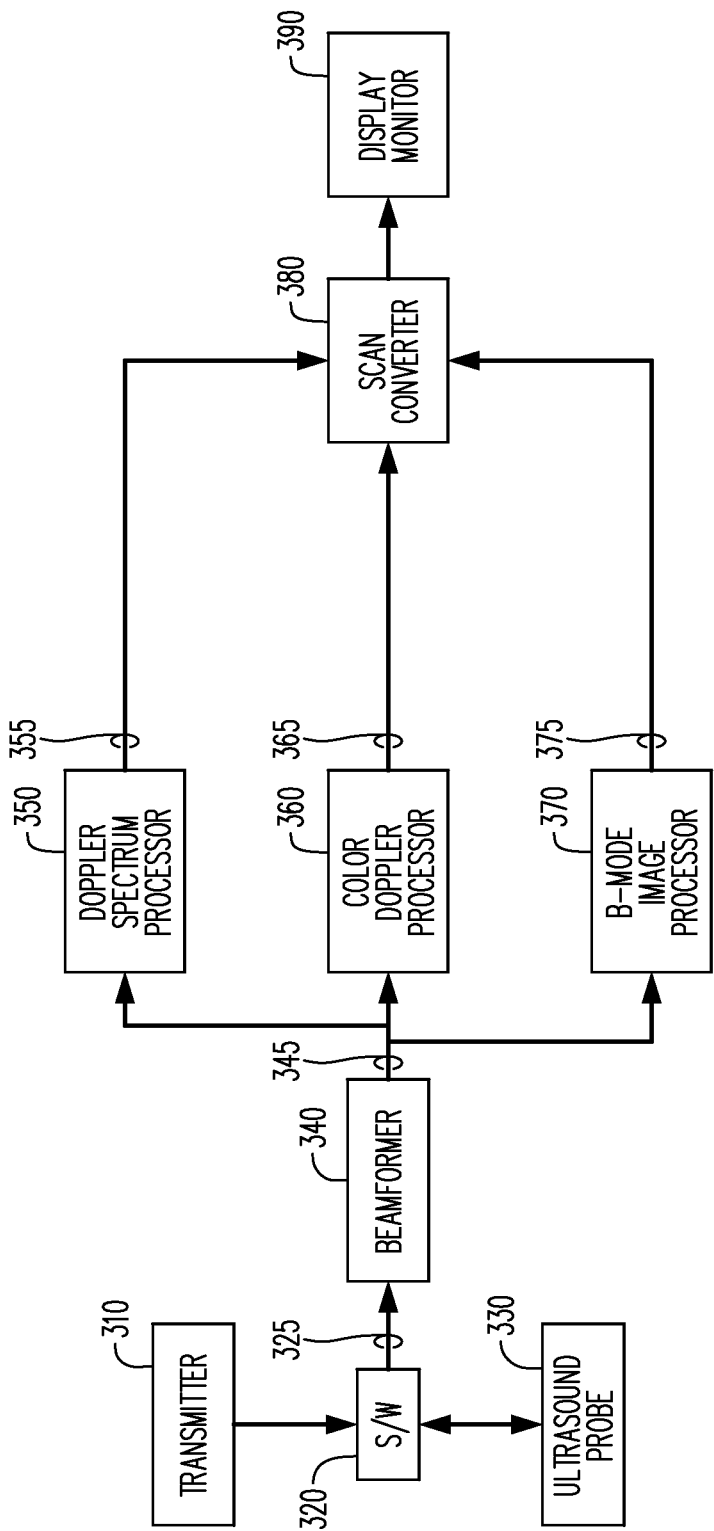
FIG. 3: A diagram of an ultrasound diagnostic imaging system (prior art).

FIG. 3 shows a diagram of a conventional ultrasound diagnostic imaging system with B-mode imaging, Doppler spectrum and color Doppler imaging (e.g., see U.S. Pat. No. 4,573,477, U.S. Pat. No. 4,622,977, U.S. Pat. No. 4,641,668, U.S. Pat. No. 4,651,742, U.S. Pat. No. 4,651,745, U.S. Pat. No. 4,759,375, U.S. Pat. No. 4,766,905, U.S. Pat. No. 4,768,515, U.S. Pat. No. 4,771,789, U.S. Pat. No. 4,780,837, U.S. Pat. No. 4,799,490, and U.S. Pat. No. 4,961,427). The system may include other imaging modes, e.g. elasticity imaging, 3D imaging, real-time 3D imaging, tissue Doppler imaging, tissue harmonic imaging, contrast imaging and others. An ultrasound signal is transmitted from an ultrasound probe 330 driven by a transmitter 310 through a transmit/receive switch 320. The probe 320 may consist of an array of transducer elements which are separately driven by the transmitter with different time-delays so that a transmit ultrasound beam is focused and steered. A beamformer 340 receives the received ultrasound signal(s) from the probe 330 through the switch 320 and processes the signal(s) 325. The beamformer applies delays and/or phases to the signals and the resultant signals are summed for focusing and steering a receive ultrasound beam. The beamformer may also apply apodization, amplification and filtering.

The processed signal 345 is coupled to a Doppler spectrum processor 350, a color Doppler processor 360, and a B-mode image processor 370. The Doppler spectrum processor 350 includes a Doppler signal processor and a spectrum analyzer, and processes Doppler flow velocity signals and calculates and outputs a Doppler spectrum 355. The color Doppler processor 360 processes the received signal 345 and calculates and outputs velocity, power and variance signals 365. The B-mode image processor 370 processes the received signal 345 and calculates and outputs a B-mode image 375 or the amplitude of the signal by an amplitude detection.

The Doppler spectrum signals 355, color Doppler processor signals (velocity, power, and variance) 365 and B-mode processor signals 375 are coupled to a scan converter 380 that converts the signals to scan-converted signals. The output of scan converter 380 is coupled to a display monitor 390 for displaying ultrasound images.

Figure 4:
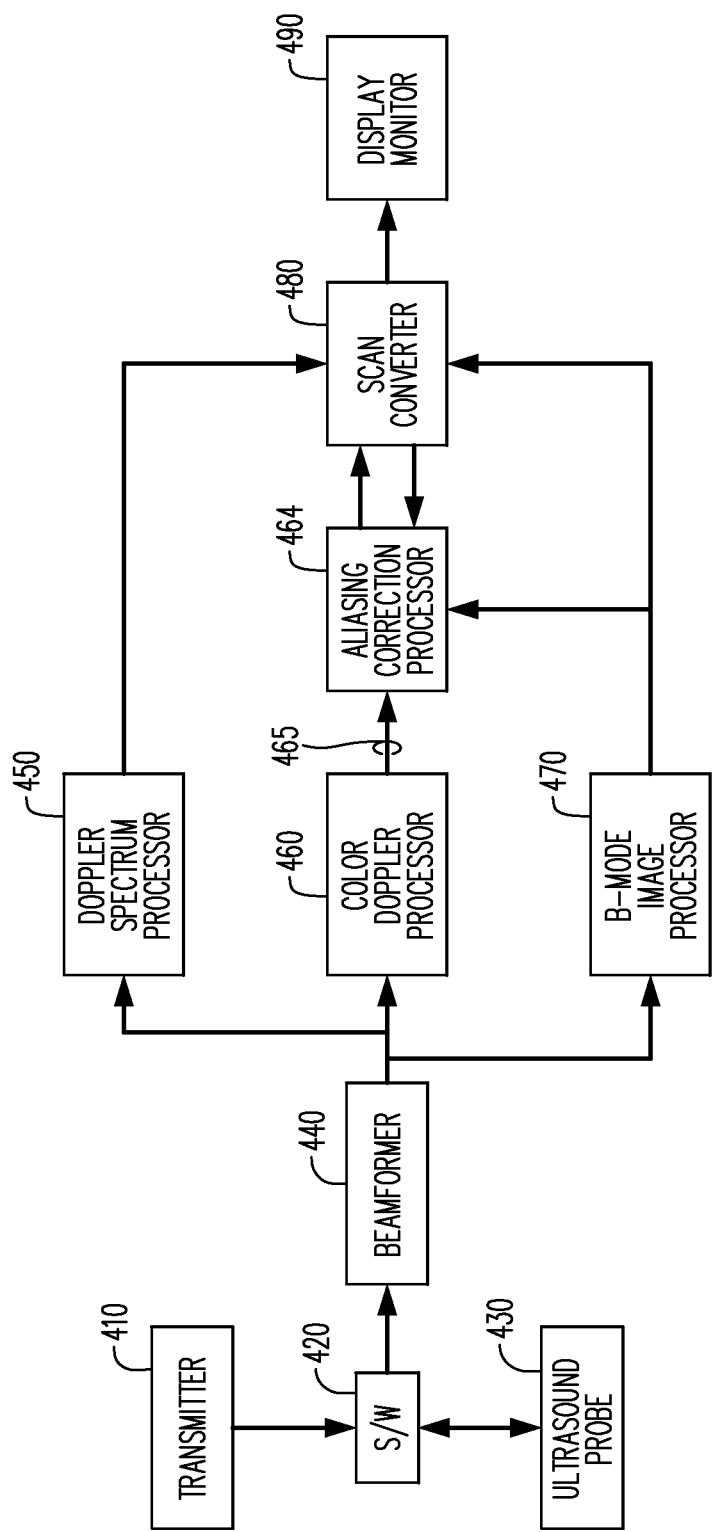
FIG. 4: A diagram of an ultrasound diagnostic imaging system according to some embodiments and using line data.
Figure 5:
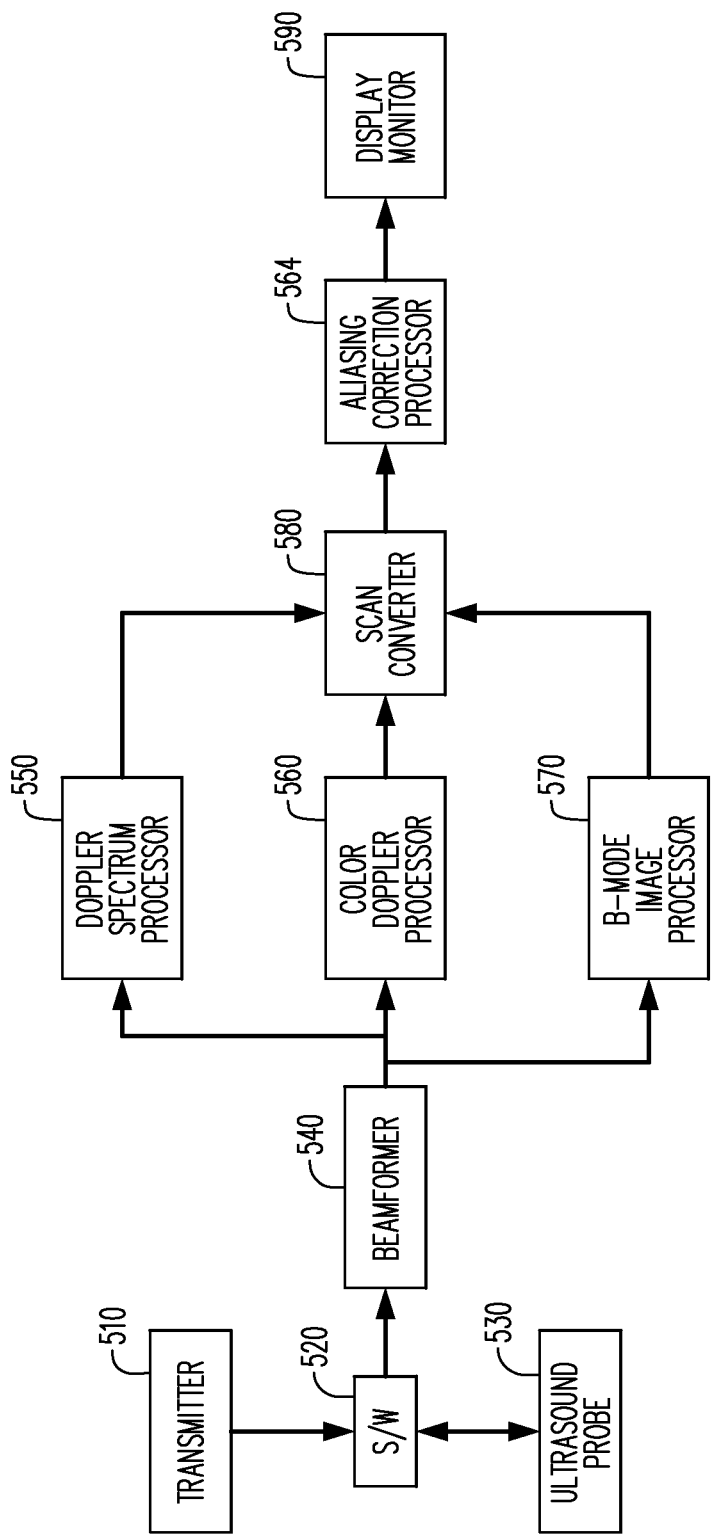
FIG. 5: A diagram of an ultrasound diagnostic imaging system according to some embodiments and using scan-converted images.

FIG. 4 shows a diagram of an ultrasound imaging system including a color Doppler aliasing correction processor 464 according to some embodiments. The aliasing correction processor 464 may perform the aliasing correction method described previously with respect to color flow line data as described above. The aliasing correction processor 464 receives output 465 from the color Doppler processor 460. Output 465 comprises color flow line data rather than the scan-converted color Doppler image. The aliasing correction processor 464 outputs correct color Doppler data after aliasing correction. FIG. 5 shows a diagram of embodiments in which the correction of color Doppler aliasing is performed in the scan-converted image domain rather than the line data domain which was discussed previously. The B-mode image and color Doppler image are scan-converted before the aliasing correction processor 564 performs processing thereon.

The aliasing correction processors 464, 564 may be comprised of general purpose central processing units (CPUs), digital signal processors (DSPs), field programmable Arrays (FPGAs), graphic processing units (GPUs) and/or discreet electronics devices.

The foregoing description references velocity, velocity aliasing and velocity aliasing corrections. However, the description may be equally applicable to the frequency domain or the phase domain via equations (1), (3) and (4). The velocity or color velocity, which is actually the velocity component v cos θ in the ultrasound beam direction as shown in equation (1), may be converted to the Doppler shift frequency via equation (1). Then, the Doppler shift frequency in turn may be converted to a phase or the color Doppler phase via equation (4). Velocity aliasing may be converted to frequency aliasing or phase aliasing. Aliasing correction may be applied to Doppler shift frequency values in the frequency domain or color Doppler phase values in the phase domain.

Color velocity, color flow velocity, color Doppler velocity, flow velocity or velocity discussed herein are directly related to the Doppler shift frequency via equation (1) and are actually the flow velocity component in the ultrasound beam direction as implied by cos θ or the projection of the true flow velocity onto the ultrasound beam direction assuming no aliasing.

The positive velocity or positive velocity direction refers to a flow that is directed toward the ultrasound transducer within a range of +/−90 degrees from the center axis of the ultrasound beam rather than away from the transducer. The negative velocity or negative velocity direction refers to flow directed away from the ultrasound transducer with a range of +/−90 degrees from the center axis of ultrasound beam.

One or more embodiments have been described. Nevertheless, various modifications will be apparent to those in the art.

What is claimed is:

1. A computer-implemented method comprising:
acquiring color Doppler data;
detecting one or more transitions of the color Doppler data, each of the one or more transitions being between a first area representing flow velocity in a first direction and a second area representing flow velocity not in the first direction;

evaluating a normalized energy function across one or more of the one or more transitions;

determining, for each flow area of the color Doppler data, whether the flow area is in contact with a zero velocity area, and whether the flow area is surrounded by and in contact with a flow area of opposite velocity direction; and determining an aliasing correction for each respective flow area of the color Doppler data based on the evaluated normalized energy functions, and based on the determination of whether the respective flow area is in contact with a zero velocity area, and the determination of whether the respective flow area is surrounded by and in contact with a flow area of opposite velocity direction.

2. A computer-implemented method according to claim 1, wherein evaluating the normalized energy function across a transition comprises:

calculating the sum of the absolute differences between each of one or more pairs of color Doppler values which are located on opposite sides of the transition; and dividing said sum of the absolute differences by the number of the one or more pairs of color Doppler values.

3. A computer-implemented method according to claim 1, wherein determining whether the flow area is surrounded by and in contact with a flow area of opposite velocity direction comprises:

determining whether the flow area is surrounded by and in contact with a second flow area of opposite velocity direction from the flow area, whether the second flow area is surrounded by and in contact with a third flow area of opposite velocity direction from the second flow area, and whether the third flow area is surrounded by and in contact with a fourth flow area of opposite velocity direction from the third flow area.

4. A computer-implemented method according to claim 1, wherein determining the aliasing corrections comprises:

determining no aliasing corrections for the color Doppler data in response to a determination that the normalized energy function across one or more transitions is less than a preset threshold.

5. A computer-implemented method according to claim 4, wherein the preset threshold is a velocity corresponding to the Doppler shift frequency of half a pulse repetition frequency associated with the color Doppler data.

6. A computer-implemented method according to claim 1, wherein determining the aliasing corrections comprises:

determining single aliasing correction for the color Doppler data of a flow area in contact with a transition in response to a determination that the normalized energy function across the transition is greater than a preset threshold.

7. A computer-implemented method according to claim 1, wherein determining the aliasing corrections comprises:

determining no aliasing correction for the color Doppler data of a flow area in contact with a zero velocity area.

8. A computer-implemented method according to claim 1, wherein determining the aliasing corrections comprises:

determining single aliasing correction for the color Doppler data of a flow area which is in contact with a zero flow area and in contact with a transition with an opposite flow velocity area, wherein the normalized energy function across the transition is greater than a preset threshold.

9. A computer-implemented method according to claim 8, wherein the flow area for which single aliasing correction is determined is smaller than the opposite flow velocity area.

10. A computer-implemented method according to claim 8, wherein determining single aliasing correction comprises:

evaluating a first total energy function of the color Doppler data based on single aliasing correction applied to one of the two flow areas (area A) and no aliasing corrections applied to the other one of the two flow areas (area B);

evaluating a second total energy function of the color Doppler data based on single aliasing correction applied to area B and no aliasing corrections applied to area A; and determining a smaller of the first and second total energy functions.

11. A computer-implemented method according to claim 1, wherein determining the aliasing corrections comprises:

determining single aliasing correction for the color Doppler data of a flow area representing flow velocity in a first direction which is surrounded by a second flow area representing flow velocity in a second direction which is in contact with a zero velocity area; and determining no aliasing correction for the color Doppler data of the second flow area.

12. A computer-implemented method according to claim 1, wherein determining the aliasing corrections comprises:

determining single aliasing correction for the color Doppler data of a first flow area representing flow velocity in a first direction which is surrounded by a second flow area representing flow velocity in a second direction which is in contact with a zero velocity area; and determining no aliasing correction for the color Doppler data of the second flow area in response to a determination that the normalized energy function across a transition between the first flow area and the second flow area is greater than a preset threshold.

13. A computer-implemented method according to claim 1, wherein determining the aliasing corrections comprises:

determining double aliasing correction for the color Doppler data of a first flow area representing flow velocity in a first direction which is surrounded by and in contact with a second flow area representing flow velocity in a second direction which is in turn surrounded by and in contact with a third flow area representing flow velocity in the first flow direction which is surrounded by and in contact with a zero velocity area;

determining single aliasing correction for the color Doppler data of the second flow area; and determining no aliasing correction for the color Doppler data of the third flow area.

14. A computer-implemented method according to claim 1, wherein, determining the aliasing corrections comprises:

determining double aliasing correction for the color Doppler data of a first flow area representing flow velocity in a first direction which is surrounded by and in contact with a second flow area representing flow velocity in a second direction which is in turn surrounded by and in contact with a third flow area representing flow velocity in the first direction which is surrounded by and in contact with a zero velocity area;

determining single aliasing correction for the color Doppler data of the second flow area; and determining no aliasing correction for the color Doppler data of the third flow area, in response to a determination that the normalized energy function across a transition between the first flow area and the second flow area is less than a first preset threshold and in response to a determination that the normalized energy function across a transition between the second flow area and the third flow area is greater than a second preset threshold.

15. A computer-implemented method according to claim 1, wherein determining the aliasing corrections comprises:
- determining no aliasing correction for the color Doppler data of a first flow area representing flow velocity in a first direction which is surrounded by and in contact with a second flow area representing flow velocity in a second direction which is surrounded by and in contact with a third flow area representing flow velocity in the first direction which is surrounded by and in contact with a zero velocity area;
- determining single aliasing correction for the color Doppler data of the second flow area; and
- determining no aliasing correction for the color Doppler data of the third flow area, in response to a determination that the normalized energy function across a transition between the first flow area and the second flow area is greater than a first preset threshold and in response to a determination that the normalized energy function across a transition between the second flow area and third flow area is greater than a second preset threshold.

16. A computer-implemented method according to claim 1, wherein determining the aliasing corrections comprises:
- determining triple aliasing correction for the color Doppler data of a first flow area representing flow velocity in a first direction which is surrounded by and in contact with a second flow area representing flow velocity in a second direction which is surrounded by and in contact with a third flow area representing flow velocity in the first direction which is surrounded by and in contact with a fourth flow area which is surrounded by and in contact with a zero velocity area;
- determining double aliasing correction for the color Doppler data of the second flow area;
- determining single aliasing correction for the color Doppler data of the third flow area; and
- determining no aliasing correction for the color Doppler data of the fourth flow area.

17. A computer-implemented method according to claim 1, wherein determining the aliasing corrections comprises:
- determining triple aliasing correction for the color Doppler data of a first flow area representing flow velocity in a first direction which is surrounded by and in contact with a second flow area representing flow velocity in a second direction which is surrounded by and in contact with a third flow area representing flow velocity in the first direction which is surrounded by and in contact with a fourth flow area which is surrounded by and in contact with a zero velocity area;
- determining double aliasing correction for the color Doppler data of the second flow area;
- determining single aliasing correction for the color Doppler data of the third flow area; and
- determining no aliasing correction for the color Doppler data of the fourth flow area, in response to a determination that the normalized energy function across a transition between the first flow area and the second flow area is greater than a preset threshold, in response to a determination that the normalized energy function across a transition between the second flow area and the third flow area is less than a second preset threshold, and in response to a determination that the normalized energy function across a transition between the third flow area and the fourth flow area is greater than a third preset threshold.

18. A computer-implemented method according to claim 1, wherein determining the aliasing corrections comprises:
- determining single aliasing correction for the color Doppler data of a first flow area representing flow velocity in a first direction which is surrounded by and in contact with a second flow area representing flow velocity in a second direction which is surrounded by and in contact with a third flow area representing flow velocity in the first flow direction which is surrounded by and in contact with a fourth flow area representing flow velocity in the second flow direction which is surrounded by and in contact with a zero velocity area;
- determining double aliasing correction for the color Doppler data of the second flow area;
- determining single aliasing correction for the color Doppler data of the third flow area; and
- determining no aliasing correction for the color Doppler data of the fourth flow area, in response to a determination that the normalized energy function across a transition between the first flow area and the second flow area is less than a preset threshold, in response to a determination that the normalized energy function across a transition between the second flow area and the third flow area is less than a second preset threshold, and in response to a determination that the normalized energy function across a transition between the third flow area and the fourth flow area is greater than a third preset threshold.

19. A method according to claim 1, wherein determining whether the flow area is surrounded by and in contact with a flow area of opposite velocity direction comprises:
- determining whether the flow area is surrounded by and in contact with a second flow area of opposite velocity direction from the flow area.

20. A method according to claim 1, wherein determining whether the flow area is surrounded by and in contact with a flow area of opposite velocity direction comprises:
- determining whether the flow area is surrounded by and in contact with a second flow area of opposite velocity direction from the flow area and whether the second flow area is surrounded by and in contact with a third flow area of opposite velocity direction from the second flow area.

21. A system comprising:
- an aliasing correction processor configured to:
- acquire color Doppler data;
- detect one or more transitions of the color Doppler data, each of the one or more transitions being between a first area representing flow velocity in a first direction and a second area representing flow velocity not in the first direction;
- evaluate a normalized energy function across one or more of the one or more transitions;
- determine, for each flow area of the color Doppler data, whether the flow area is in contact with a zero velocity area, and whether the flow area is surrounded by and in contact with a flow area of opposite velocity direction; and
- determine an aliasing correction for each respective flow area of the color Doppler data based on the evaluated normalized energy functions, and based on the determination of whether the respective flow area is in contact with a zero velocity area, and the determination of whether the respective flow area is surrounded by and in contact with a flow area of opposite velocity direction.

22. A system according to claim 21, wherein evaluation of the normalized energy function across a transition comprises:

calculation of the sum of the absolute differences between each of one or more pairs of color Doppler values which are located on opposite sides of the transition; and division of said sum of the absolute differences by the number of the one or more pairs of color Doppler values.

23. A system according to claim 21, wherein determination of whether the flow area is surrounded by and in contact with a flow area of opposite velocity direction comprises:

determination of whether the flow area is surrounded by and in contact with a second flow area of opposite velocity direction from the flow area, whether the second flow area is surrounded by and in contact with a third flow area of opposite velocity direction from the second flow area, and whether the third flow area is surrounded by and in contact with a fourth flow area of opposite velocity direction from the third flow area.

24. A system according to claim 21, wherein determination of the aliasing corrections comprises:

determination of no aliasing corrections for the color Doppler data in response to a determination that the normalized energy function across one or more transitions is less than a preset threshold.

25. A system according to claim 24, wherein the preset threshold is a velocity corresponding to the Doppler shift frequency of half a pulse repetition frequency associated with the color Doppler data.

26. A system according to claim 21, wherein determination of the aliasing corrections comprises:

determination of single aliasing correction for the color Doppler data of a flow area in contact with a transition in response to a determination that the normalized energy function across the transition is greater than a preset threshold.

27. A system according to claim 21, wherein determination of the aliasing corrections comprises:

determination of no aliasing correction for the color Doppler data of a flow area in contact with a zero velocity area.

28. A system according to claim 21, wherein determination of the aliasing corrections comprises:

determination of single aliasing correction for the color Doppler data of a flow area which is in contact with a zero flow area and in contact with a transition with an opposite flow velocity area, wherein the normalized energy function across the transition is greater than a preset threshold.

29. A system according to claim 28, wherein the flow area for which single aliasing correction is determined is smaller than the opposite flow velocity area.

30. A system according to claim 28, wherein determination of single aliasing correction comprises:

evaluation of a first total energy function of the color Doppler data based on single aliasing correction applied to one of the two flow areas (area A) and no aliasing corrections applied to the other one of the two flow areas (area B);

evaluation of a second total energy function of the color Doppler data based on single aliasing correction applied to area B and no aliasing corrections applied to area A; and determination of a smaller of the first and second total energy functions.

31. A system according to claim 21, wherein determination of the aliasing corrections comprises:

determination of single aliasing correction for the color Doppler data of a flow area representing flow velocity in a first direction which is surrounded by a second flow area representing flow velocity in a second direction which is in contact with a zero velocity area; and determination of no aliasing correction for the color Doppler data of the second flow area.

32. A system according to claim 21, wherein determination of the aliasing corrections comprises:

determination of single aliasing correction for the color Doppler data of a first flow area representing flow velocity in a first direction which is surrounded by a second flow area representing flow velocity in a second direction which is in contact with a zero velocity area; and determination of no aliasing correction for the color Doppler data of the second flow area in response to a determination that the normalized energy function across a transition between the first flow area and the second flow area is greater than a preset threshold.

33. A system according to claim 21, wherein determination of the aliasing corrections comprises:

determination of double aliasing correction for the color Doppler data of a first flow area representing flow velocity in a first direction which is surrounded by and in contact with a second flow area representing flow velocity in a second direction which is in turn surrounded by and in contact with a third flow area representing flow velocity in the first flow direction which is surrounded by and in contact with a zero velocity area;

determination of single aliasing correction for the color Doppler data of the second flow area; and determination of no aliasing correction for the color Doppler data of the third flow area.

34. A system according to claim 21, wherein, determination of the aliasing corrections comprises:

determination of double aliasing correction for the color Doppler data of a first flow area representing flow velocity in a first direction which is surrounded by and in contact with a second flow area representing flow velocity in a second direction which is in turn surrounded by and in contact with a third flow area representing flow velocity in the first direction which is surrounded by and in contact with a zero velocity area;

determination of single aliasing correction for the color Doppler data of the second flow area; and determination of no aliasing correction for the color Doppler data of the third flow area, in response to a determination that the normalized energy function across a transition between the first flow area and the second flow area is less than a first preset threshold and in response to a determination that the normalized energy function across a transition between the second flow area and the third flow area is greater than a second preset threshold.

35. A system according to claim 21, wherein determination of the aliasing corrections comprises:

determination of no aliasing correction for the color Doppler data of a first flow area representing flow velocity in a first direction which is surrounded by and in contact with a second flow area representing flow velocity in a second direction which is surrounded by and in contact with a third flow area representing flow velocity in the first direction which is surrounded by and in contact with a zero velocity area;

determination of single aliasing correction for the color Doppler data of the second flow area; and determination of no aliasing correction for the color Doppler data of the third flow area, in response to a determination that the normalized energy function across a transition between the first flow area and the second flow area is greater than a first preset threshold and in response to a determination that the normalized energy function across a transition between the second flow area and third flow area is greater than a second preset threshold.

36. A system according to claim 21, wherein determination of the aliasing corrections comprises:
   determination of triple aliasing correction for the color Doppler data of a first flow area representing flow velocity in a first direction which is surrounded by and in contact with a second flow area representing flow velocity in a second direction which is surrounded by and in contact with a third flow area representing flow velocity in the first direction which is surrounded by and in contact with a fourth flow area which is surrounded by and in contact with a zero velocity area;
   determination of double aliasing correction for the color Doppler data of the second flow area;
   determination of single aliasing correction for the color Doppler data of the third flow area; and
   determination of no aliasing correction for the color Doppler data of the fourth flow area.

37. A system according to claim 21, wherein determination of the aliasing corrections comprises:
   determination of triple aliasing correction for the color Doppler data of a first flow area representing flow velocity in a first direction which is surrounded by and in contact with a second flow area representing flow velocity in a second direction which is surrounded by and in contact with a third flow area representing flow velocity in the first direction which is surrounded by and in contact with a fourth flow area which is surrounded by and in contact with a zero velocity area;
   determination of double aliasing correction for the color Doppler data of the second flow area;
   determination of single aliasing correction for the color Doppler data of the third flow area; and
   determination of no aliasing correction for the color Doppler data of the fourth flow area, in response to a determination that the normalized energy function across a transition between the first flow area and the second flow area is greater than a preset threshold, in response to a determination that the normalized energy function across a transition between the second flow area and the third flow area is less than a second preset threshold, and in response to a determination that the normalized energy function across a transition between the third flow area and the fourth flow area is greater than a third preset threshold.

38. A system according to claim 21, wherein determination of the aliasing corrections comprises:
   determination of single aliasing correction for the color Doppler data of a first flow area representing flow velocity in a first direction which is surrounded by and in contact with a second flow area representing flow velocity in a second direction which is surrounded by and in contact with a third flow area representing flow velocity in the first flow direction which is surrounded by and in contact with a fourth flow area representing flow velocity in the second flow direction which is surrounded by and in contact with a zero velocity area;
   determination of double aliasing correction for the color Doppler data of the second flow area;
   determination of single aliasing correction for the color Doppler data of the third flow area; and
   determination of no aliasing correction for the color Doppler data of the fourth flow area, in response to a determination that the normalized energy function across a transition between the first flow area and the second flow area is less than a preset threshold, in response to a determination that the normalized energy function across a transition between the second flow area and the third flow area is less than a second preset threshold, and in response to a determination that the normalized energy function across a transition between the third flow area and the fourth flow area is greater than a third preset threshold.

39. A system according to claim 21, wherein determination of whether the flow area is surrounded by and in contact with a flow area of opposite velocity direction comprises:
   determination of whether the flow area is surrounded by and in contact with a second flow area of opposite velocity direction from the flow area.

40. A system according to claim 21, wherein determination of whether the flow area is surrounded by and in contact with a flow area of opposite velocity direction comprises:
   determination of whether the flow area is surrounded by and in contact with a second flow area of opposite velocity direction from the flow area and whether the second flow area is surrounded by and in contact with a third flow area of opposite velocity direction from the second flow area.

* * * * *